United States Patent [19]

Yamada et al.

[11] Patent Number: 5,247,070
[45] Date of Patent: Sep. 21, 1993

[54] N-TERMINAL MUTEINS OF TUMOR NECROSIS FACTOR

[75] Inventors: Nobutoshi Yamada; Masanari Kato; Keizo Miyata; Yoshiyuki Aoyama; Hiroshi Shikama, all of Kusatsu, Japan

[73] Assignee: Ishihara Sangyo Kaisha Ltd., Osaka, Japan

[21] Appl. No.: 763,512

[22] Filed: Sep. 20, 1991

[30] Foreign Application Priority Data

Sep. 21, 1990 [JP] Japan ............... 2-250045
Jun. 17, 1991 [JP] Japan ............... 3-240130

[51] Int. Cl.$^5$ ............................ C07K 13/00
[52] U.S. Cl. ..................... 530/351; 530/402; 530/395; 424/85.1; 930/144; 435/69.5; 435/69.7
[58] Field of Search ............ 530/351, 402, 395; 424/85.1; 930/144; 435/69.5, 69.7

[56] References Cited

U.S. PATENT DOCUMENTS 4,677,063  6/1987  Mark et al. ............ 530/351
5,095,096  3/1942  Miki et al. ............ 530/351

FOREIGN PATENT DOCUMENTS 291804  11/1988  European Pat. Off.
8809344  12/1988  World Int. Prop. O.

OTHER PUBLICATIONS

Biochemistry, 3rd ed, 1988, Stryer, pp. 277-278.
Biochem, vol. 27(24) 1988, pp. 8780-8787, (abstract only).
Cell, vol. 59(5) 1989, pp. 905-913 (abstract only).
Nippon Kyobu Shikkan Gakkai Zasshi, vol. 30(3), 1992, pp. 402-406 (abstract only).

Primary Examiner—Garnette D. Draper
Attorney, Agent, or Firm—Oblon, Spivak, McClelland, Maier & Neustadt

[57] ABSTRACT

A polypeptide which is a tumor necrosis factor polypeptide having an amino acid sequence represented by from the 1st Ser to the 155th Leu as shown by SEQ ID NO:1 in the Sequence Listing, or its mutein, wherein the amino acid sequence of the 1st Ser to the 8th Asp of the SEQ ID NO:1 or the corresponding amino acid sequence of the mutein is replaced by an amino acid sequence containing at least one amino acid sequence of cell-adherent peptide of laminin and from 5 to 30 amino acids. Also disclosed are a recombinant plasmid containing a DNA encoding such a polypeptide, a recombinant microbial cell transformed by such a recombinant plasmid, a process for producing the polypeptide, a pharmaceutical composition comprising the polypeptide as an active ingredient, and a DNA for the polypeptide.

12 Claims, 15 Drawing Sheets

[ NOTE ] * SYMBOL INDICATES THE REPLACED BASES

1. MOLECULAR WEIGHT MARKER OF PROTEIN
2. F4616 / FINALLY PURIFIED SAMPLE
3. F4617 / FINALLY PURIFIED SAMPLE

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 155 amino acids
( B ) TYPE: amino acid
( D ) TOPOLOGY: linear ( i i ) MOLECULE TYPE: protein ( x ) PUBLICATION INFORMATION:
( A ) AUTHORS: Pennica, et al
( C ) JOURNAL: Nature
( D ) VOLUME: 312
( F ) PAGES: 724-
( G ) DATE: 1984

( x i ) SEQUENCE DESCRIPTION: SEQ ID NO:1:

| | | | | | | | | | | | | | | | |
|---|---|---|---|---|---|---|---|---|---|---|---|---|---|---|---|
| Ser | Ser | Ser | Arg | Thr | Pro | Ser | Asp | Lys | Pro | Val | Ala | His | Val | Val | Ala |
| 1 | | | | 5 | | | | | 10 | | | | | 15 | |
| Asn | Pro | Gln | Ala | Glu | Gly | Gln | Leu | Gln | Trp | Leu | Asn | Arg | Arg | Ala | Asn |
| | | | 20 | | | | | 25 | | | | | 30 | | |
| Ala | Leu | Leu | Ala | Asn | Gly | Val | Glu | Leu | Arg | Asp | Asn | Gln | Leu | Val | Val |
| | | 35 | | | | | 40 | | | | | 45 | | | |
| Pro | Ser | Glu | Gly | Leu | Tyr | Leu | Ile | Tyr | Ser | Gln | Val | Leu | Phe | Lys | Gly |
| | 50 | | | | | 55 | | | | | 60 | | | | |
| Gln | Gly | Cys | Pro | Ser | Thr | His | Val | Leu | Leu | Thr | His | Thr | Ile | Ser | Arg |
| 65 | | | | | 70 | | | | | 75 | | | | | 80 |
| Ile | Ala | Val | Ser | Tyr | Gln | Thr | Lys | Val | Asn | Leu | Leu | Ser | Ala | Ile | Lys |
| | | | | 85 | | | | | 90 | | | | | 95 | |
| Ser | Pro | Cys | Gln | Arg | Glu | Thr | Pro | Glu | Gly | Ala | Glu | Ala | Lys | Pro | Trp |
| | | | 100 | | | | | 105 | | | | | 110 | | |
| Tyr | Glu | Pro | Ile | Tyr | Leu | Gly | Gly | Val | Phe | Gln | Leu | Glu | Lys | Gly | Asp |
| | | 115 | | | | | 120 | | | | | 125 | | | |
| Arg | Leu | Ser | Ala | Glu | Ile | Asn | Arg | Pro | Asp | Tyr | Leu | Asp | Phe | Ala | Glu |
| | 130 | | | | | 135 | | | | | 140 | | | | |
| Ser | Gly | Gln | Val | Tyr | Phe | Gly | Ile | Ile | Ala | Leu | | | | | |
| 145 | | | | | 150 | | | | | 155 | | | | | |

( 2 ) INFORMATION FOR SEQ ID NO:2:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( x i ) SEQUENCE DESCRIPTION: SEQ ID NO:2:

| | | | | | | | | | | | | | | |
|---|---|---|---|---|---|---|---|---|---|---|---|---|---|---|
| Asp | Gly | Tyr | Ile | Gly | Ser | Arg | Ser | Ser | Ser | Arg | Ala | Pro | Ser | Asp |
| 1 | | | | 5 | | | | | 10 | | | | | 15 |

( 2 ) INFORMATION FOR SEQ ID NO:3:

( i ) SEQUENCE CHARACTERISTICS:

(A) LENGTH: 17 amino acids
(B) TYPE: amino acid
(D) TOPOLOGY: linear (ii) MOLECULE TYPE: peptide (xi) SEQUENCE DESCRIPTION: SEQ ID NO:3:

| Cys | Asp | Pro | Gly | Tyr | Ile | Gly | Ser | Arg | Ser | Ser | Ser | Arg | Ala | Pro | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Asp (2) INFORMATION FOR SEQ ID NO:4:

(i) SEQUENCE CHARACTERISTICS:
(A) LENGTH: 11 amino acids
(B) TYPE: amino acid
(D) TOPOLOGY: linear (ii) MOLECULE TYPE: peptide (xi) SEQUENCE DESCRIPTION: SEQ ID NO:4:

| Ser | Ser | Tyr | Ile | Gly | Ser | Arg | Thr | Pro | Ser | Asp |
|-----|-----|-----|-----|-----|-----|-----|-----|-----|-----|-----|
| 1   |     |     |     | 5   |     |     |     |     | 10  |     |

(2) INFORMATION FOR SEQ ID NO:5:

(i) SEQUENCE CHARACTERISTICS:
(A) LENGTH: 13 amino acids
(B) TYPE: amino acid
(D) TOPOLOGY: linear (ii) MOLECULE TYPE: peptide (xi) SEQUENCE DESCRIPTION: SEQ ID NO:5:

| Tyr | Ile | Gly | Ser | Arg | Ser | Ser | Ser | Arg | Ala | Pro | Ser | Asp |
|-----|-----|-----|-----|-----|-----|-----|-----|-----|-----|-----|-----|-----|
| 1   |     |     |     | 5   |     |     |     |     | 10  |     |     |     |

(2) INFORMATION FOR SEQ ID NO:6:

(i) SEQUENCE CHARACTERISTICS:
(A) LENGTH: 18 amino acids
(B) TYPE: amino acid
(D) TOPOLOGY: linear (ii) MOLECULE TYPE: peptide (xi) SEQUENCE DESCRIPTION: SEQ ID NO:6:

| Tyr | Ile | Gly | Ser | Arg | Tyr | Ile | Gly | Ser | Arg | Ser | Ser | Ser | Arg | Ala | Pro |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Ser Asp (2) INFORMATION FOR SEQ ID NO:7:

(i) SEQUENCE CHARACTERISTICS:
(A) LENGTH: 465 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:7:

```
TCATCTTCTC GAACCCCGAG TGACAAGCCT GTAGCCCATG TTGTAGCAAA CCCTCAAGCT      60
GAAGGGCAGC TCCAGTGGCT GAACCGCCGG GCCAATGCCC TCCTGGCTAA TGGAGTGGAG     120
CTCAGAGATA ACCAACTAGT GGTGCCATCA GAGGGCCTGT ACCTGATCTA CTCTCAGGTC     180
CTCTTCAAGG GTCAAGGCTG CCCATCCACC CATGTGCTCC TCACCCACAC CATCAGCCGC     240
ATCGCCGTCT CCTACCAGAC CAAGGTTAAC CTCCTCTCTG CTATTAAGAG CCCCTGCCAG     300
```

| AGGGAGACCC | CCGAGGGCGC | AGAGGCCAAG | CCCTGGTATG | AGCCCATCTA | TCTGGGAGGG | 360 |
| GTCTTTCAAC | TGGAGAAGGG | TGACCGACTC | AGCGCTGAGA | TCAATCGGCC | CGACTATCTC | 420 |
| GACTTTGCCG | AGTCTGGGCA | GGTCTACTTT | GGGATCATTG | CCCTG | | 465 |

(2) INFORMATION FOR SEQ ID NO:8:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

| AATTCATGTG | CGACCCCGGG | TACATTGGAA | GCAGATCTTC | ATC | 43 |

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

| AATTCATGTA | CATTGGAAGC | A | 21 |

(2) INFORMATION FOR SEQ ID NO:10:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

| AATTCATGTA | TATCGGTTCA | CGATACATTG | GAAGCA | 36 |

(2) INFORMATION FOR SEQ ID NO:11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

| GATCCCGGGC | GCGGAGATTC | TCCCTCATCT | TC | 32 |

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

| ATGTCATCTT | ATATTGGTTC | TCGAACC | 27 |

N-TERMINAL MUTEINS OF TUMOR NECROSIS FACTOR

BACKGROUND OF THE INVENTION

1. Field of the Invention

The present invention is concerned with providing a novel polypeptide which is a human TNF N-terminal mutein and relates to the polypeptide itself, a pharmaceutical composition containing the polypeptide, a process for producing the polypeptide, a recombinant DNA sequence encoding the polypeptide, a plasmid containing the recombinant DNA sequence and a transformed microbial cell having the plasmid.

2. Discussion of Background

TNF (tumor necrosis factor alpha) is a physiologically active compound, which was found to be present in the serum of a mouse preliminarily transfected with *Bacillus Calmette Guerin* (BCG) and treated by endotoxin, by Carswell et al. in 1975 (*Proc. Natl. Acad. Sci. USA*, 72, 3666 (1975)). In 1984, cDNA of human TNF was cloned by Pennica et al., and the entire primary structure (amino acid sequence) of the human TNF protein was clarified (*Nature*, 312, 724 (1984)). TNF has specific antitumor effects such as a cytotoxic activity against tumor cells and hemorrhagia necrosis or growth inhibition against transplanted tumor. However, it has been reported recently that side effects such as hyperlipemia, hypotension or fever, are likely to result from the administration of TNF. Accordingly, many research and development efforts are being made to obtain a product superior in the activity as compared to TNF, while exhibiting reduced side effects. For example, Japanese Unexamined Patent Publications No. 40221/1986 (equivalent to U.S. Pat. No. 4,650,674, incorporated herein by reference), No. 119692/1988 (equivalent to U.S. Pat. No. 4,990,455, incorporated herein by reference) and No. 277488/1989 (equivalent to European patent Publication No. EP-A-340,333, incorporated herein by reference) disclose deletion of one or more certain specific amino acid residues in the human TNF protein, replacement thereof by other amino acid residues or addition thereto of other amino acid residues, to provide a human TNF mutein.

However, it has not yet been possible to obtain a human TNF mutein having fully satisfactory pharmacological effects.

SUMMARY OF THE INVENTION

Accordingly, it is an object of the present invention to provide a novel human TNF N-terminal mutein having antitumor effects similar to human TNF or its mutein and being free of side effects associated with TNF.

It is another object of the present invention to provide a human TNF N-terminal mutein, having antitumor effects similar to human TNF or a mutein thereof, which is free of the side effect of promoting metastasis as observed with human TNF or muteins thereof. It is another object of the present invention to provide a method for preparing such human TNF N-terminal muteins. It is another object of the present invention to provide pharmaceutical compositions containing such human TNF N-terminal muteins. It is another object of the present invention to provide recombinant DNA sequences which encode such human TNF N-terminal muteins. It is another object of the present invention to provide plasmids which contain such recombinant DNA sequences. It is another object of the present invention to provide transformed microbial cells which have such plasmids. These and other objects, which will become apparent during the following detailed description, have been achieved by a polypeptide which is a tumor necrosis factor polypeptide or a mutein thereof, wherein the amino acid sequence from the Ser residue at position 1 ($^1$Ser) to the Asp residue at position 8 ($^8$Asp) of the tumor necrosis factor polypeptide or the corresponding amino acid sequence of said mutein is replaced by an amino acid sequence containing at least one amino acid sequence of a cell-adherent peptide of laminin and from 5 to 30 amino acids.

The present inventors have found it possible to obtain a novel human TNF N-terminal mutein polypeptide which has substantially the same antitumor activity as human TNF or mutein thereof, but which does not substantially promote tumor metastasis, as observed with human TNF or its known muteins. The novel human TNF N-terminal mutein polypeptides of the present invention are obtained by incorporating an amino acid sequence of cell-adherent peptide of laminin at a certain amino acid sequence domain of the amino acid sequence of human TNF or a mutein thereof. The present invention has been accomplished on the basis of this discovery.

In other words, the present invention relates to a polypeptide which is a tumor necrosis factor polypeptide having an amino acid sequence represented by the sequence from the 1st Ser to the 155th Leu as shown by SEQ ID NO:1 in the Sequence Listing, or a mutein thereof, wherein the amino acid sequence of the 1st Ser to the 8th Asp of said SEQ ID NO:1 or the corresponding amino acid sequence of said mutein is replaced by an amino acid sequence containing at least one amino acid sequence of cell-adherent peptide of laminin and from 5 to 30 amino acids, wherein said polypeptide is from 137 to 192 amino acid residues long and has the antitumor activity of human tumor necrosis factor and the amino acid sequence of said polypeptide, other than the sequence replacing the sequence corresponding to the 1st Ser to the 8th Asp, corresponds to the sequence of the 9th Lys to the 155th Leu in SEQ ID NO:1 in which up to 15 additions, deletions, substitutions or combinations thereof of amino acid residues have been made.

The present invention also provides recombinant plasmids containing a DNA sequence encoding such a polypeptide, microbial cells transformed by such a recombinant plasmid, a process for producing a polypeptide by such a microbial cell, pharmaceutical compositions containing such a polypeptide, a polypeptide having methionine bonded to the N-terminal of such a polypeptide, and a DNA sequence encoding for a tumor necrosis factor polypeptide, wherein the nucleotide sequence from the 1st to 3rd TCA (1st codon) to the 22nd to 24th GAC (8th codon) in SEQ ID NO:7 or the corresponding nucleotide sequence of a mutant DNA thereof is replaced by a nucleotide sequence coding for an amino acid sequence containing at least one amino acid sequence of cell-adherent peptide of laminin and from 5 to 30 amino acids, wherein said polypeptide is from 137 to 192 amino acid residues long and has the antitumor of human tumor necrosis factor and the amino acid sequence of said polypeptide, other than the sequence replacing the sequence corresponding to the 1st Ser to the 8th Asp, corresponds to the sequence of the 9th Lys to the 155th Leu in SEQ ID NO:1 in which up to 15 additions, deletions, substitutions or combinations thereof of amino acid residues have been made.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
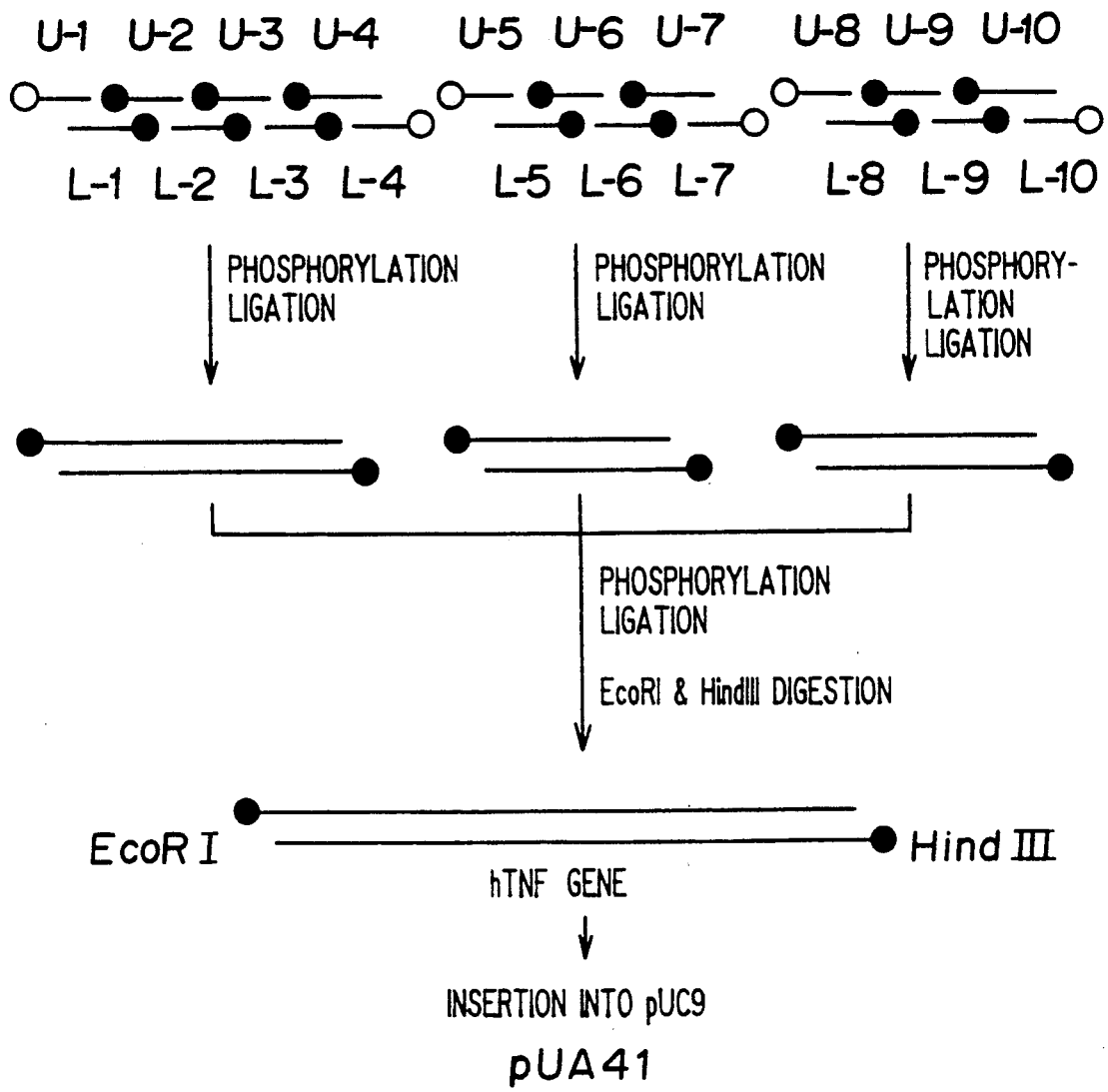
FIG. 1 illustrates the process steps for cloning a human TNF gene by ligation of synthetic oligonucleotides.

The tumor necrosis factor polypeptide having an amino acid sequence represented by the sequence from the 1st Ser to the 155th Leu as shown by SEQ ID NO:1 in the Sequence Listing represents human TNF.

In the present invention, the term "the mutein of human TNF" and the term "human TNF or a mutein thereof" include a mutein obtained by applying a single or combined treatment of modifications such as addition, deletion and replacement of one or more amino acids, suitably to the amino acid sequence as shown by SEQ ID NO:1 in the Sequence Listing and having antitumor effects similar to human TNF. Such muteins may be obtained by recombinant DNA techniques. Accordingly, in the present invention, the amino acid sequence of said mutein corresponding to the amino acid sequence of from the 1st Ser to the 8th Asp of SEQ ID NO:1, corresponds to the amino acid sequence after modification, in a case where the above amino acid sequence is modified in the mutein. This modification includes deletion of one or more amino acids and thus includes partial or entire deletion of the amino acid sequence of from the 1st Ser to the 8th Asp.

Specifically, the human TNF mutein includes, for example, the following, but the present invention is not limited to such specific examples.

(1) As disclosed in Japanese Unexamined Patent Publication No. 141999/1988 (U.S. Pat. No. 4,948,875):

To the N-terminal, Val-Arg is added, and further, $^{29}$Arg-$^{30}$Arg is changed to $^{29}$Asn-$^{30}$Thr.

(2) As disclosed in Japanese Unexamined Patent Publication No. 119692/1988 (U.S. Pat. No. 4,990,455):

(A) $^{32}$Asn is changed to $^{32}$Tyr, $^{32}$His, $^{32}$Asp or $^{32}$Ser.

(B) $^{115}$Pro is changed to $^{115}$Leu, $^{115}$Ser, $^{115}$Asp or $^{115}$Gly.

(C) $^{117}$Tyr is changed to $^{117}$His.

(3) As disclosed in Japanese Unexamined Patent Publication No. 277488/1989 (EP-A-340,333):

$^1$Ser to $^8$Asp are deleted, and Arg-Lys-Arg is added to the N-terminal of $^9$Lys.

(4) As disclosed in Japanese Unexamined Patent Publication No. 163094/1990 (WO-90-03395):

$^1$Ser to $^8$Asp are deleted, and Arg-Lys-Arg is added to the N-terminal of $^9$Lys, and $^{154}$Ala is changed to $^{154}$Phe.

(5) As disclosed in Japanese Unexamined Patent Publication No. 142493/1990 (WO-90-03395):

$^1$Ser to $^8$Asp are deleted, Arg-Lys-Arg is added to the N-terminal of $^9$Lys, and $^{154}$Ala is changed to 154Trp.

(6) As disclosed in Japanese Unexamined Patent Publication No. 270697/1988:

$^{100}$Gln to $^{107}$Ala are deleted.

From $^1$Ser, from 2 to 8 amino acid residues are deleted.

(7) As disclosed in Japanese Patent Application No. 193935/1990:

$^{68}$Pro is changed to $^{68}$Asp, $^{68}$Met or $^{68}$Tyr.

(8) As disclosed in Japanese Patent Application No. 311129/1990: $^{106}$Gly is deleted or replaced by another amino acid.

(9) As disclosed in Japanese Patent Application No. 311130/1990: $^{29}$Arg is replaced by another amino acid.

Throughout the specification, symbols in the following list are used to represent amino acids, polypeptides, bases or their sequences.

Amino acids

Symbols: Ala, Cys, Asp,
Meaning: alanine, cysteine, aspartic acid,
Symbols: Glu, Phe, Gly,
Meaning: glutamic acid, phenylalanine, glycine,
Symbols: His, Ile, Lys, Leu,
Meaning: histidine, isoleucine, Lysine, Leucine,
Symbols: Met, Asn, Pro,
Meaning: methionine, asparagine, proline,
Symbols: Gln, Arg, Ser, Thr,
Meaning: glutamine, arginine, serine, threonine,
Symbols: Val, Trp, Tyr
Meaning: valine, tryptophan, tyrosine When used in a polypeptide sequence, these symbols represent amino acid residues, rather than free amino acids.

Bases

Symbols: A, C, G, T, U

Meaning: adenine, cytosine, guanine, thymine, uracil

When used in a DNA sequence, these symbols represent deoxyribonucleic acid residues rather than free molecules such as adenosine phosphate or free bases such as adenine.

Further, various abbreviations used in the specification have the following meanings.

dATP: Deoxy adenosine triphosphate
dGTP: Deoxy guanosine triphosphate
dCTP: Deoxy cytidine triphosphate
TTP: Thymidine triphosphate
ATP: Adenosine triphosphate
SDS: Sodium dodecyl sulfate
BPB: Bromophenol Blue
DTT: Dithiothreitol
BSA: Bovine serum albumin
PMSF: Phenylmethylsulfonyl fluoride
EDTA: Ethylenediaminetetraacetic acid
CPG resin: Controlled-Pore Glass resin The amino acid sequence having the amino acid sequence of cell-adherent peptide of laminin may be composed solely of said amino acid sequence of cell-adherent peptide of laminin, but may otherwise be composed of such amino acid sequence of cell-adherent peptide of laminin and one or more additional amino acids. Further, it may have one or more such amino acid sequence of cell-adherent peptide of laminin. The number of amino acids constituting the amino acid sequence having the amino acid sequence of cell-adherent peptide of laminin is from 5 to 30. Specifically, the amino acid sequences shown respectively by SEQ ID NOS:2 to 6 in the Sequence Listing or others may be mentioned. Among them, the amino acid sequence shown by SEQ ID NO: 2, 3 or 4 is particularly preferred.

The amino acid sequence of cell-adherent peptide of laminin is preferably an amino acid sequence represented by from the 3rd Tyr to the 7th Arg in the amino acid sequence shown by SEQ ID NO:2 in the Sequence Listing.

The sequence of the present polypeptides, other than the amino acid sequence replacing the sequence corresponding to the 1st Ser to the 8th Asp, corresponds substantially to the sequence from the 9th Lys to the 155th Leu in SEQ ID NO:1 and may contain up to 15 additions, deletions or substitutions of amino acid residues or combinations thereof. The sequence other amino acid sequence of cell-adherent peptide of laminin and from 5 to 30 amino acids, of the polypeptide N-terminal mutein of the present invention, is preferably an amino acid sequence of human TNF represented by the sequence from the 9th Lys to the 155th Leu of SEQ ID NO:1, or such an amino acid sequence having the 29th Arg, the 68th Pro or the 106th Gly deleted or replaced by another amino acid residue. Such another amino acid residue is preferably Gln, Lys, Asp, Val or Leu for the 29th Arg; it is preferably Asp or Met for the 68th Pro; and it is preferably Trp, Pro, Ala, Asp or Arg for the 106th Gly.

Thus, the present polypeptide N-terminal mutein is suitably from 137 to 192 amino acid residues long.

The DNA for a tumor necrosis factor polypeptide having a nucleotide sequence represented by the 1st T to the 465th G as shown by SEQ ID NO:7 in the Sequence Listing, is one form of DNA encoding the amino acid sequence of human TNF. The mutational DNA of a DNA encoding the amino acid sequence of human TNF, is a DNA obtained by applying a single or composite treatment of modifications such as addition, deletion and replacement of one or more sets of codons appropriately to the nucleotide sequence as shown by SEQ ID NO:7 in the Sequence Listing and encoding the amino acid sequence of the above-mentioned human TNF mutein. Accordingly, such modifications are applicable to the entire region of the nucleotide sequence represented by the 1st T to the 465th G as shown by SEQ ID NO:7. Namely, such modifications are applicable not only to the nucleotide sequence of from the 1st T to the 24th C, but also to the nucleotide sequence of from the 25th A to the 465th G.

Now, the present invention will be described in detail with reference to Examples. For the gene manipulation involved in the present invention, conventional methods and techniques disclosed in many references may be employed with suitable adjustments. Some of such references will be listed below.

T. Maniatis et al., (1982): *Molecular Cloning, A Laboratory Manual* (hereinbelow, referred to simply as Molecular Cloning), Cold Spring Harbor Laboratory, R. Wu et al., (1983): *Methods in Enzymology*, 100 and 101, R. Wu et al., (1987): *Methods in Enzymology*, 153, 154 and 155

The polypeptide of the present invention can be produced by various methods, by means of various techniques and equipments. A typical method for its production will now be described.

(1) Designing of a human TNF gene

As mentioned above, the nucleotide sequence of a human TNF gene and the amino acid sequence of the human TNF have been clarified by Pennica et al., and the nucleotide sequence is changed as the case requires to design the human TNF gene sequence. The sequence is designed for DNA double strands wherein the DNA strand of SEQ ID NO:7 is the upper strand (i.e. the coding strand) and the corresponding complementary strand is the lower strand. At that time, it is preferred to select codons suitable for the host cell (such as *Escherichia coli*), and it is further preferred to provide restriction endonuclease cleavage sites at appropriate positions to facilitate the gene modification for the preparation of a mutein and to facilitate the cloning by ligating DNA fragments as described hereinafter. It is of course necessary to provide a translation initiation codon (ATG) 25 at the 5'-side and a translation termination codon (TAA, TGA or TAG) at the 3'-side of the human TNF gene respectively. Further, it is preferred to provide appropriate restriction endonuclease cleavage sites upstream of the translation initiation codon and downstream of the translation termination codon, respectively, to improve the applicability to a vector and to facilitate the cloning. Here, the preparation is based on the above-mentioned DNA double-strands. The upper (coding or sense) strand contains 474 bases (hereinafter referred to as a coding 474U strand) having 5'-ATG-3' joined in an upstream direction to the 1st T and having 5'-TAATGA-3' joined in a downstream direction to the 465th G. Accordingly, the lower strand (hereinafter referred to as a complementary 474L strand) contains 474 bases starting from T and ending at T, as described below the upper strand, and is complementary to the coding 474U strand.

The human TNF gene can be prepared by a method wherein each of the upper and lower strands is divided into a plurality of oligonucleotides, such a plurality of oligonucleotides are chemically synthesized, and blocks of such synthesized oligonucleotides are then sequentially appropriately ligated. For example, in the case of DNA double-strands prepared on the basis of the DNA double-strands comprising the coding 474U strand and the complementary 474L strand, each of the strands for the human TNF gene is divided into ten oligonucleotides each comprising about 50 bases, and a total of twenty oligonucleotides are chemically synthesized.

As the method for such synthesis, a diester method (H. G. Khorana, "Some Recent Developments in Chemistry of Phosphate Esters of Biological Interest", John Wiley and Sons, Inc., New York (1961)), a triester method (R. L. Letsinger et al., J. Am. Chem. Soc., 89, 4801 (1967)), or a phosphite method (M. D. Matteucci et al., Tetrahedron Lett., 21, 719 (1980)) may be mentioned. However, in view of the operation efficiency, it is preferred to employ a phosphite method using a completely automated DNA synthesizer.

Synthesized oligonucleotides are then purified by a conventional purification method, such as high performance chromatography using a reversed phase chromatography column, or electrophoresis, using polyacrylamide gel. Thereafter, the oligonucleotides are phosphorylated by means of, e.g., T4 polynucleotide kinase, then annealed and ligated by means of T4 DNA ligase. Here, the oligonucleotides are divided into several blocks and sequentially ligated so that the human TNF gene sequence will eventually be obtained, followed by digestion with restriction endonucleases or polishing (make blunt-end) with T4 DNA polymerase, and the resulting DNA fragments are then purified by electrophoresis. The obtained DNA fragments are inserted into plasmid vectors such as pUC8, pUC9, pUC18 and pUC19 (J. Messing et al., Gene, 19, 259 (1982)), and the inserted plasmid vectors are introduced into competent cells for cloning in accordance with a usual method. From the obtained clones, plasmid DNAs are extracted and purified by a usual method, and they are examined to see whether or not the nucleotide sequences of the DNA fragments inserted into the vectors agree with the desired gene sequence. The respective sections of the human TNF gene thus obtained, are then cut out from the plasmid vectors containing them, by means of restriction endonucleases, then ligated and inserted again into the above vector to obtain a plasmid vector having the desired full length of the human TNF gene. The plasmid vector thus obtained is digested by restriction endonucleases and separated and purified by gel electrophoresis to obtain the desired human TNF gene.

On the other hand, a method which comprises preparing cDNA encoding human TNF from mRNA derived from human cells expressing TNF and using such cDNA, may be used in combination with the above described method, as the case requires.

(2) Cloning of human TNF expression vector

The human TNF gene obtained in the above step (1) is appropriately inserted into an expression vector to clone a human TNF expression vector. The expression vector is required to have a promoter and a SD (Shine-Dalgano) sequence upstream of the translation initiation codon (ATG) and a terminator downstream of the translation termination codon (TAA, TGA or TAG). As the promoter, trp promoter, lac promoter, tac promoter, $P_L$ promoter, $\beta$-lactamase promoter, $\alpha$-amylase promoter, PH05 promoter, or ADCI promoter may be suitably used, and as the terminator, trp terminator, rrnB terminator or ADCI terminator may be suitably used. Such an expression vector is readily available among commercial products such as pKK223-3 (Pharmacia), $pP_L$-lambda (Pharmacia) and pDR720 (Pharmacia). However, such commercial products may further be improved for use to have better expression properties or handling efficiency.

(3) Cloning of human TNF mutein or N-terminal mutein expression vector

The following methods may, for example, be employed for the preparation of DNA encoding the human TNF mutein or N-terminal mutein polypeptide.

(A) In the same manner as the method described in the above step (1) for designing the human TNF gene, chemically synthesized oligonucleotides are appropriately ligated to obtain such a mutant DNA. According to this method, modification such as the replacement, addition or deletion of a codon or codons encoding an amino acid, an oligopeptide or a polypeptide, can freely be performed.

(B) The human TNF gene prepared in the above step (1) is cut by appropriate restriction endonucleases to remove 5 a certain specific region in the gene, and then a synthetic oligonucleotide having a nucleotide sequence with a mutation introduced (for example: a double-stranded DNA fragment prepared by annealing the upper and lower strands and ligating them) or an appropriate other gene is inserted. The modification can freely be performed also by this method in the same manner as in the above method (A).

(C) Introduction of a mutation is conducted by extending the DNA strand by using, as a primer, a synthesized oligonucleotide having a nucleotide sequence with the mutation introduced [site directed mutagenesis method (T. A. Kunkel et al., Methods in Enzymology, 154, 367 (1987))]. This method is not suitable for addition or insertion of a relatively long DNA chain exceeding ten base pairs. However, other modifications can freely be performed in the same manner as in the above method (A). This method is suitable, particularly for replacing any desired amino acids.

In the present invention, the site directed mutagenesis method (C) and the method (B) of using the fragments cut by restriction endonucleases, are usually used in combination, as the case requires. Such a method will be described below.

(i) By the site directed mutagenesis method, DNA encoding a mutein or N-terminal mutein polypeptide is prepared and suitably inserted into an expression vector.

Firstly, to conduct the site directed mutagenesis method, template DNA is prepared. The human TNF gene obtained in the above step (1) is ligated to a plasmid vector (such as pUC118 or pUC119) for the preparation of a single-stranded plasmid DNA developed by Messing et al. (Methods in Enzymology, 153, 3 (1987)), and then introduced into Escherichia coli. From the transformant thereby obtained, a clone having the desired plasmid is selected This plasmid is introduced into a dut⁻ and ung⁻ E. coli mutant (such as a CJ236 strain) to have uracil taken in the gene, and the E. coli mutant is infected with a recombinant helper phage such as M13K07 to obtain the desired single stranded plasmid DNA.

On the other hand, an oligonucleotide primer with from about 15 to 50 bases having the mutation introduction site and the forward and backward base sequences thereof according to the present invention, is chemically synthesized. This primer and the uracil-introduced single-stranded plasmid DNA obtained by the previous step, are annealed and then double-stranded by means of e.g. T4 DNA polymerase and T4 DNA ligase. The double stranded plasmid is introduced into a ung+ *E. coli* strain, to deactivate the DNA strand containing uracil as a template and thereby to improve the frequency for introduction of the mutation.

Using the above primer as a probe, colony hybridization is conducted, whereupon a clone having a plasmid containing DNA encoding the desired mutein or N-terminal mutein polypeptide, is selected from the obtained transformants.

From the plasmid thus obtained, a DNA fragment encoding the human TNF mutein or N-terminal mutein polypeptide, is cut out by restriction endonucleases and inserted into an expression vector in the same manner as in the case of the above step (2) to clone the desired human TNF mutein or N-terminal mutein expression vector.

(ii) A section to which a mutation is to be introduced, is cut out by suitable restriction endonucleases and substituted by a DNA fragment prepared by, e.g., chemical synthesis in accordance with the modification design, to obtain an expression vector of the mutein or N-terminal mutein polypeptide.

To modify the amino acid sequence in the vicinity of the N-terminal of human TNF, it is preferred that there exists a suitable restriction endonuclease cleavage site in the vicinity of the N-terminus. Therefore, a suitable restriction endonuclease cleavage site is introduced near the N-terminus of human TNF by the site directed mutagenesis. It is further preferred to provide two types of cleavage sites i.e. this restriction endonuclease cleavage site and a restriction endonuclease cleavage site provided before or after the translation initiation codon located upstream thereof.

On the other hand, in accordance with the modification design of the present invention, oligonucleotides corresponding to the upper (coding) and lower (noncoding) strands are chemically synthesized in the same manner as in the case of the above step (1). It is, of course, necessary to provide the above-mentioned restriction endonuclease cleavage sites at both termini in consideration of the insertion into an expression vector. Such oligonucleotides (the upper and lower strands) are phosphorylated by means of, e.g., T4 polynucleotide kinase, followed by annealing, to obtain a double-stranded DNA fragment. This double-stranded DNA fragment is inserted and ligated by means of, e.g., T4 DNA ligase in the expression plasmid vector containing the majority of human TNF digested by the above-mentioned two types of restriction endonucleases (with the N-terminal portion deleted), to obtain the desired expression vector of the human TNF N-terminal mutein having the amino acid sequence near the N-terminus modified.

By using appropriate restriction endonuclease cleavage sites in the gene encoding the mutein or N-terminal mutein polypeptide, recombination among the respective expression vectors may be conducted to produce further expression vectors for novel mutein or N-terminal mutein polypeptides.

Introduction of an expression vector into host cells such as cells of a *E. coli* strain can be conducted by a conventional method, such as a method of employing competent cells of an *E. coli* strain prepared by a calcium chloride method (*Molecular Cloning*, T. Maniatis et al., (1982)). As such host cells, microbial cells such as *Escherichia coli*, *Bacillus* or yeast can be used. Among them, as *Escherichia coli*, mutants of a *E. coli* K-12 strain such as JM83, JM103 and HB101, may be mentioned.

(4) Preparation of human TNF N-terminal mutein polypeptide

In the present invention, the transformed microbial cells disclosed in the above step (3) are cultured, whereby the desired human TNF N-terminal mutein polypeptide will be produced and accumulated in the culture, and the accumulated polypeptide is then extracted and separated. As a method for culturing the microbial cells, particularly cells of *Escherichia coli*, a conventional method may be employed such as a method wherein *Escherichia coli* is inoculated to a medium containing nutrients requested by *Escherichia coli*, and cultured in a large amount in a short period of time usually by shaking or stirring the inoculated medium at a temperature of from 32° to 37° C. for from 12 to 24 hours. As the medium, L-broth, M9 medium or M9CA medium (see the above-mentioned Molecular Cloning) may, for example, be used. If necessary, an antibiotic such as ampicillin may be added, and in order to improve the efficiency of the promoter, it is possible to add a reagent such as isopropyl-$\beta$-D-thiogalactopyranoside in the case where lac promoter or tac promoter is used, or a reagent such as 3-$\beta$ -indole acrylic acid in the case where trp promoter is used, at the initiation of culturing or during the culturing.

The human TNF N-terminal mutein polypeptide of the present invention is obtained usually by sonicating microbial cells after culturing, in a suspended state in Tris-buffer, followed by centrifugal separation to remove debris. The product thus obtained may further be purified by treatment with nucleic acid endotoxin removing agent, filtration by a filter, anion exchange chromatography or any other conventional protein-separation and purification method.

By applying the above-described methods appropriately, the human TNF N-terminal mutein gene of the present invention can be produced directly, or can be produced after the preparation of the human TNF gene, or can be produced after preparing the human TNF gene, followed by preparation of its mutein gene.

The human TNF N-terminal mutein polypeptide of the present invention has the same antitumor activity as human TNF or a mutein thereof, while being free of metastatis-promoting side effect. While it shows antitumor activities at the same level as human TNF or its mutein, it shows no substantial activity for promoting metastasis of tumor which is observed with human TNF or its mutein. Therefore, it is effective as an active ingredient for an antitumor agent or pharmaceutical. Specific examples of the human TNF N-terminal mutein polypeptide of the present invention include, for example, F4236, F4146, F4419, F4422, F4423, F4603, F4604, F4616, 4617, 4630, 4631, 4636, F4637, F4618, F4619, F4632, F4633, F4640, F4641, F4620, F4621, F4622, F4623, F4624, F4647, F4648, F4649, F4650 and F4651 which will be described hereinafter. Among them, F4236, F4146, F4419, F4603, F4616, and F4617 are preferred, and F4236, F4146 and F4419 are particularly preferred. To prepare its pharmaceutical compositions containing the present polypeptide, the present polypeptide can be formulated into pharmaceutical compositions together with pharmaceutically acceptable carriers or diluents. The types of the pharmaceutical compositions of the present invention include agents for external application, agents for oral administration and agents for injection. The pharmaceutical compositions are administered by administration methods suitable for the respective formulations.

As the administration method, injection is preferred. The injection includes systemic injection and local injection. The systemic injection includes intravenous injection, subcutaneous injection, intramuscular injection and intradermal injection. The pharmaceutical composition of the present invention may be applied to any method. However, the systemic injection is preferred taking into consideration the applicability to various cancer species. Further, from the nature of the drug, intravenous injection is particularly preferred. The cancer species include solid tumors such as colorectal cancer, lung cancer, gastric cancer, pancreatic cancer and melanoma, and leukemia. The pharmaceutical composition of the present invention may be applied to any cancer species. However, it is particularly preferred to apply it to a solid tumor.

Having generally described the invention, a further understanding can be obtained by reference to certain specific examples, which are provided herein for purposes of illustration only and are not intended to be limiting unless otherwise specified.

EXAMPLE 1

Designing of human TNF gene

On the basis of the amino acid sequence of the human TNF structural gene already reported by Pennica et al. as mentioned above, a nucleotide sequence of DNA double-strands, i.e. coding 474U strand and complementary 474L strand, in the DNA strand sequence of SEQ ID NO:7 in the Sequential Listing and a nucleotide sequence of such DNA double-strands with a certain modification, were designed for the convenience of gene cloning and mutein preparation with respect to the nucleotide sequence of the human TNF gene. Here, restriction endonuclease cleavage sites were inserted at appropriate intervals. Further, in order to facilitate the ligation to a plasmid vector, a cleavage site by restriction endonuclease EcoR I was provided upstream of a translation initiation codon (ATG), and a cleavage site by restriction endonuclease Hind III was provided downstream of a translation termination codon (TAA and TGA).

EXAMPLE 2

Chemical synthesis of oligonucleotides

The DNA designed in Example 1 was chemically synthesized by a phosphite method by means of an automatic DNA synthesizer (Model 381A, manufactured by Applied Biosystems). After dividing the designed DNA into twenty oligonucleotides of U-1 to U-10 and L-1 to L-10 having nucleotide sequences as described hereinafter, they were synthesized.

These oligonucleotides will be described with reference to the DNA strand shown by SEQ ID NO:7 in the Sequence Listing.

U-1: Comprises 27 bases and has a sequence of from the 1st T to the 19th A of SEQ ID NO:7, and yet has a sequence in which 5'-ATG-3' is joined upstream of the 1st T and 5'-AATTC-3' is joined upstream thereof.

U-2: Comprises 50 bases and has a sequence of from the 20th G to the 69th G of SEQ ID NO:7.

U-3: Comprises 49 bases and has a sequence of from the 70th C to the 118th G of SEQ ID NO:7.

U-4: Comprises 50 bases and has a sequence of from the 119th A to the 168th C of SEQ ID NO:7.

U-5: Comprises 50 bases and has a sequence of from the 169th T to the 218th T of SEQ ID NO:7.

U-6: Comprises 52 bases and has a sequence of from the 219th C to the 270th C of SEQ ID NO:7.

U-7: Comprises 48 bases and has a sequence of from the 271st C to the 318th C of SEQ ID NO:7.

U-8: Comprises 49 bases and has a sequence of from the 319th G to the 367th C of SEQ ID NO:7.

U-9: Comprises 51 bases and has a sequence of from the 368th A to the 418th C of SEQ ID NO:7.

U-10: Comprises 53 bases and has a sequence of from the 419th T to the 465th G of SEQ ID NO:7, and further has 5'-TAATGA-3' downstream thereof.

The lower strand (complementary strand) corresponding to the DNA strand of SEQ ID NO:7 will be described. However, the description of the flow direction of the lower strand (5'- and 3'-) will be reversed from that of the upper strand.

L-1: Comprises 29 bases and has a sequence complementary to the sequence of from the 25th A to the 1st T of SEQ ID NO:7, and yet has a sequence having 5'-CATG-3' joined to the 3'-side of A complementary to the 1st T of the upper strand.

L-2: Comprises 52 bases and has a sequence complementary to the sequence of from the 77th G to the 26th A of SEQ ID NO:7.

L-3: Comprises 50 bases and has a sequence complementary to the sequence of from the 127th G to the 78th G of SEQ ID NO:7.

L-4: Comprises 50 bases and has a sequence complementary to the sequence of from the 177th G to the 128th A of SEQ ID NO:7.

L-5: Comprises 49 bases and has a sequence complementary to the sequence of from the 226th C to the 178th G of SEQ ID NO:7.

L-6: Comprises 49 bases and has a sequence complementary to the sequence of from the 275th T to the 227th A of SEQ ID NO:7.

L-7: Comprises 51 bases and has a sequence complementary to the sequence of from the 326th C to the 276th C of SEQ ID NO:7.

L-8: Comprises 49 bases and has a sequence complementary to the sequence of from the 375th G to the 327th C of SEQ ID NO:7.

L-9: Comprises 51 bases and has a sequence complementary to the sequence of from the 426th T to the 376th A of SEQ ID NO:7.

L-10: Comprises 49 bases and has a sequence complementary to the sequence of from the 465th G to the 427th G of SEQ ID NO:7, and yet has a sequence having 5'-TCATTA-3' joined to the 5'-side of C complementary to the 465th G and having 5'-AGCT-3' joined to the 5'-side thereof.

Cleavage of the synthesized oligonucleotide from the CPG resin (sold by Funakoshi Company) and removal of the protecting groups were conducted in accordance with the Mannual of Applied Biosystems, Inc. The separation and purification of each oligonucleotide was conducted by HPLC (high performance liquid chromatography) employing a reversed phase chromatocolumn or by 7M urea-containing polyacrylamide gel electrophoresis (gel concentration: 10-20%).

With respect to the HPLC method, separation and purification were conducted by eluting with a acetonitrile-containing triethylamino acetic acid (100 mM) buffer (pH7.0) by means of a reversed chromatography using a Nucleosil 5C18 column ($\phi$4.6×150 mm, sold by Chemco Scientific Co., Ltd.). The elution was conducted at a linear concentration gradient of acetonitrile of from 5 to 35% (30 minutes), and a peak of about 15 minutes was recovered.

With respect to the polyacrylamide gel electrophoresis, the respective synthesized oligonucleotide samples were separated by electrophoresis, and the band portion having the desired size was cut out as a result of the observation of the migration pattern by a UV-shadowing method, and the polyacrylamide gel fragment was cut into a size of about 1 to 2 mm$^3$, and about 2 ml of an eluting buffer (0.5M NH$_4$OAc and 1 mM EDTA) was added, and the mixture was shaked overnight at 37° C. The eluted buffer solutions containing the respective oligonucleotides were recovered, followed by phenol extraction (using a 50% phenol/50% chloroform solution) and isobutanol extraction, and ethanol precipitation operation to obtain purified samples of the respective oligonucleotides.

With respect to some of the oligonucleotides thus synthesized and purified, it was confirmed by a Maxam-Gilbert method (A. M. Maxam et al, *Methods in Enzymology*, 65, 499 (1980)) that they had the desired nucleotide sequences.

In the following gene recombination operations (Examples 3, 4, 5, 6, 7, 8, 9, 10, 11, 12 and 13), the reaction conditions, etc. of restriction endonucleases and other related enzymes were mainly in accordance with the method disclosed in the above-mentioned "Molecular Cloning". Further, the above enzymes, etc. were available mainly from Takara Shuzo, and the manual of Takara Shuzo was also used as a reference.

EXAMPLE 3

Cloning of a human TNF gene by ligation of synthesized oligonucleotides (1) Firstly, cloning of a human TNF gene was tried in accordance with FIG. 1. The synthesized oligonucleotides obtained in Example 2 were divided into three groups (U- and L-1 to 4, U- and L-5 to 7 and U- and L-8 to 10) for cloning. Namely, the 5'-terminus of each (1-2 $\mu$g) of oligonucleotides U-2, 3, 4, 6, 7, 9 and 10 and L-1, 2, 3, 5, 6, 8 and 9 was separately phosphorylated by means of from 2 to 5 units of T4 polynucleotide kinase (Takara Shuzo). The phosphorylation reaction was conducted at 37° C. for one hour in 10 $\mu$l of an aqueous solution (50 mM Tris HCl pH 7.6, 10 mM MgCl$_2$, 0.1 mM Spermidine, 0.1 mM EDTA, 10 mM DTT and 1 mM ATP), and after the reaction, T4 polynucleotide kinase was deactivated by treatment at 70° C. for 10 minutes. Separately, 10 $\mu$l of aqueous solutions of the same compositions as above which contained from 1 to 2 $\mu$g of oligonucleotides U-1, 5 and 8 and L-4, 7 and 10 respectively, were prepared. The aqueous solutions of oligonucleotides with the same U- and L-numbers (U-1 to 10 and L-1 to 10) were mixed, respectively (20 $\mu$l), and the respective mixtures were boiled at 100° C. for 5 minutes, followed by gradual cooling for annealing. Then, the obtained ten annealed fragments (double stranded DNA fragments) were divided into the above groups, and the fragments in each group were added to an aqueous solution for a ligation reaction (66 mM Tris-HCl pH 7.6, 6.6 mM MgCl$_2$, 10 mM DTT, 1 mM ATP 100 $\mu$g/ml BSA) (total amount: 120-160 $\mu$l), and the solution was heated to 40° C. and then gradually cooled for annealing. Then, 700 units of T4 DNA ligase (Takara Shuzo) was added thereto, and the ligation reaction was conducted at 16° C. for 15 hours.

After completion of the reaction, the respective reaction solutions were separated by polyacrylamide gel electrophoresis (gel concentration: 6%). From the results of observing the migration patterns by the Ethidium Bromide Staining method, the band portions having the desired sizes (176 bp, 150 bp and 153 bp) were cut out, and the desired three DNA fragments were recovered by an electro-elution method. Further, the recovered samples were subjected to phenol extraction (using a 50% phenol/50% chloroform solution) and isobutanol extraction, followed by an ethanol precipitation operation to purify the desired DNAs. The three double stranded DNA fragments thus purified, in accordance with the above-mentioned method, were phosphorylated respectively at their 5'-termini by means of T4 polynucleotide kinase, and then they were mixed in an aqueous solution for a ligation reaction, then annealed at 40° C. and ligated by an addition of T4 DNA ligase. The ligated DNA was recovered by an ethanol precipitation operation and then dissolved in 50 $\mu$l of a high salt buffer (50 mM Tris-HCl pH 7.5, 100 mM NaCl, 10 mM MgCl$_2$) containing 1 mM of DTT and 100 $\mu$g/ml of BSA. Then, a digestion reaction was conducted at 37° C. for two hours by an addition of 15 units of restriction endonuclease EcoR I (Takara Shuzo) and 15 units of restriction endonuclease Hind III (Takara Shuzo). After completion of the reaction, the desired DNA fragment (about 480 bp) was separated and purified by polyacrylamide gel electrophoresis (gel concentration: in accordance with the above-mentioned method.

On the other hand, 5 $\mu$g of plasmid vector pUC9 (obtained from Research Laboratory for Genetic Information of Kyushu University) was digested with restriction endonuclease EcoR I and Hind III in accordance with the above method, and a DNA fragment of about 2.7 Kbp was separated and purified by agarose gel electrophoresis (gel concentration: 1%). This pUC9 fragment and the previously purified DNA fragment of about 480 bp (containing the human TNF gene) were mixed in 20 $\mu$l of a ligation reaction solution, and a ligation reaction was conducted at 16° C. for 3 hours by an addition of 350 units of T4 DNA ligase. Competent cells of *E. coli* K-12 JM83 strain (obtained from Research Laboratory for Genetic Information of Kyushu University) prepared by a calcium chloride method (see *Molecular Cloning*) were transformed with the above-mentioned ligation reaction mixture in accordance with a conventional method (see Molecular Cloning).

From the ampicillin resistant clone thus obtained, a plasmid was prepared by a conventional method, and it was treated with restriction endonucleases (EcoR I and Hind III) in accordance with the above-mentioned method, and then its migration pattern was analyzed by agarose gel electrophoresis to examine the insertion of the human TNF gene into the pUC9 vector. As a result, insertion of the gene of about 250 bp was confirmed. With respect to the clone, the nucleotide sequence of the inserted gene was examined by a dideoxy method (F. Sanger, *Science*, 214, 1205 (1981)), whereby it was confirmed to be a gene fragment having the nucleotide sequence of the desired human TNF gene with a size of about 130 bp downstream from the EcoR I site and a size of about 90 bp upstream from the Hind III site. The clone and the plasmid were designated as pUA41/JM83 and pUA41, respectively.

Figure 2:
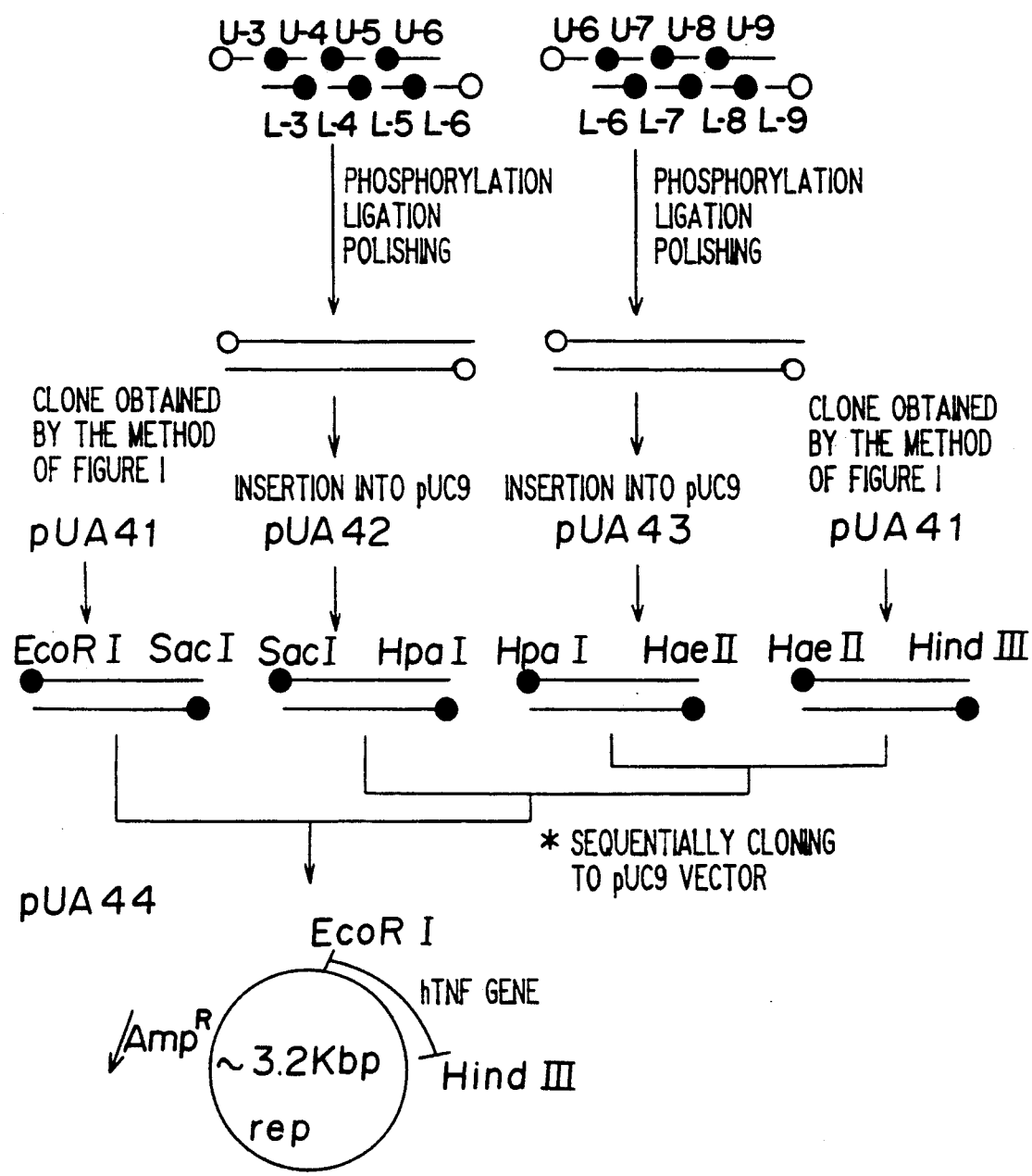
FIG. 2 illustrates the process steps for cloning a human TNF gene by ligation of synthetic oligonucleotides.

(2) Then, cloning of a human TNF gene was tried in accordance with FIG. 2.

In the nucleotide sequence of the human TNF gene, the region which was not accomplished by the cloning in the above step (1), was divided into two groups (U- and L-3 to 6 and U- and L-6 to 9), and in the same manner as in the above step (1), the oligonucleotides U-4 to 6 and U-7 to 9 and L-3 to 5 and L-6 to 8 were 5'-phosphorylated, then the two groups were annealed and ligated by means of T4 DNA ligase. The products were separated and purified by polyacrylamide gel electrophoresis (gel concentration: 6%) in accordance with the above-mentioned method, and two DNA fragments thereby obtained (201 bp and 200 bp) were respectively dissolved in 100 μl of aqueous solutions containing 67 mM of Tris-HCl (pH8.8), 6.7 mM of MgCl$_2$, 16.6 mM of (NH$_4$)$_2$SO$_4$, 6.7 μM of EDTA, 1 mM of DTT, 200 μg/ml of BSA and 330 μM of each of deoxyribonucleotide triphosphates (dATP, dGTP, dCTP and TTP), and from 2 to 5 units of T4 DNA polymerase (Takara Shuzo) was added. The mixture was reacted at 37° C. for 30 minutes to polish both termini of the DNA fragments. After completion of the reaction, the mixture was treated at 68° C. for 10 minutes to deactivate the T4 DNA polymerase, and the desired two DNA fragments were recovered by precipitation with ethanol.

On the other hand, 5 μg of pUC9 vector was dissolved in 50 μl of a medium salt buffer (10 mM Tris-HCl pH 7.5, 50 mM NaCl and 10 mM MgCl$_2$) containing 1 mM of DTT and 100 μg/ml of BSA, and 15 units of restriction endonuclease Hinc II (Takara Shuzo) was added thereto. The mixture was reacted at 37° C. for two hours, and then the vector was recovered by precipitation with ethanol. Into the cut and ring-opened pUC9 vector thus obtained, the previously polished and recovered two DNA fragments were, respectively, inserted by means of T4 DNA ligase in accordance with the above-mentioned method, whereby the *E. coli* K-12 JM83 strain was transformed. With respect to the respective clones thereby obtained, the nucleotide sequences of the inserted DNA were examined in the same manner as in the above step (1) to confirm that they were the desired nucleotide sequences. These clones were designated as pUA42/JM83 and pUA43/JM83, respectively, and the plasmids were designated as pUA42 and pUA43, respectively.

The pUA41 obtained in the above step (1) was digested with restriction endonuclease EcoR I (high salt buffer) and Sac I (low salt buffer, manufactured by Takara Shuzo) and restriction endonuclease Hae II (Takara Shuzo) and Hind III (medium salt buffer); the pUA42 obtained in the above step (2) was digested with restriction endonuclease Sac I (low salt buffer) and Hpa I (KCl buffer, manufactured by Takara Shuzo); and the pUA43 was digested with restriction endonuclease Hpa I and Hae II (KCl buffer), respectively, in accordance with the above-mentioned method. With respect to the combination of the low salt buffer (10 mM Tris-HCl pH7.5 and 10 mM MgCl$_2$) and the high salt buffer or the KCl buffer (20 mM Tris-HCl pH8.5, 100 mM KCl and 10 mM MgCl$_2$), the digestion reaction was conducted twice separately, and the precipitation operation with ethanol was conducted in between the two reactions. EcoR I-Sac I DNA fragment (127 bp) and Hae II-Hind III DNA fragment (80 bp) from the pUA41, Sac I-Hpa I DNA fragment (147 bp) from the pUA42 and Hpa I-Hae II DNA fragment (126 bp) from the pUA43 were, respectively, separated and purified by polyacrylamide gel electrophoresis (gel concentration: 6%) in accordance with the above-mentioned method.

On the other hand, 5 μg of a pUC19 plasmid vector (obtained from Research Laboratory for Genetic Information of Kyushu University) was digested with restriction endonuclease EcoR I and Hind III in accordance with the above-mentioned method, and a DNA fragment of about 2.7 Kbp was separated and purified by agarose gel electrophoresis (gel concentration: 1%). As illustrated (FIG. 2), the previously purified four DNA fragments were sequentially added and ligated thereto by means of T4 DNA ligase in accordance with the above-mentioned method, and finally inserted into the above purified pUC19 vector (fragment of about 2.7 Kbp), whereby the JM83 strain was transformed. With respect to the plasmid contained in this transformant, the nucleotide sequence of the inserted gene was examined in accordance with the above-mentioned method, whereby it was confirmed to be a clone having a plasmid vector (about 3.2 Kbp) containing the desired human TNF gene of full length (about 480 bp). This clone was designated as pUA44/JM83, and the plasmid was designated as pUA44.

EXAMPLE 4

Cloning of a human TNF expression vector (1) The following improvements were applied to expression vector pKK 223-3 (obtained from Pharmacia) having a tac promoter so that the vector can more easily be handled.

(A) To lower the molecular weight of the expression vector.

(B) To make the cleavage site by restriction endonuclease BamH I unique.

(C) To make the direction of the tac promoter opposite to the direction of the ampicillin resistant gene.

Figure 3:
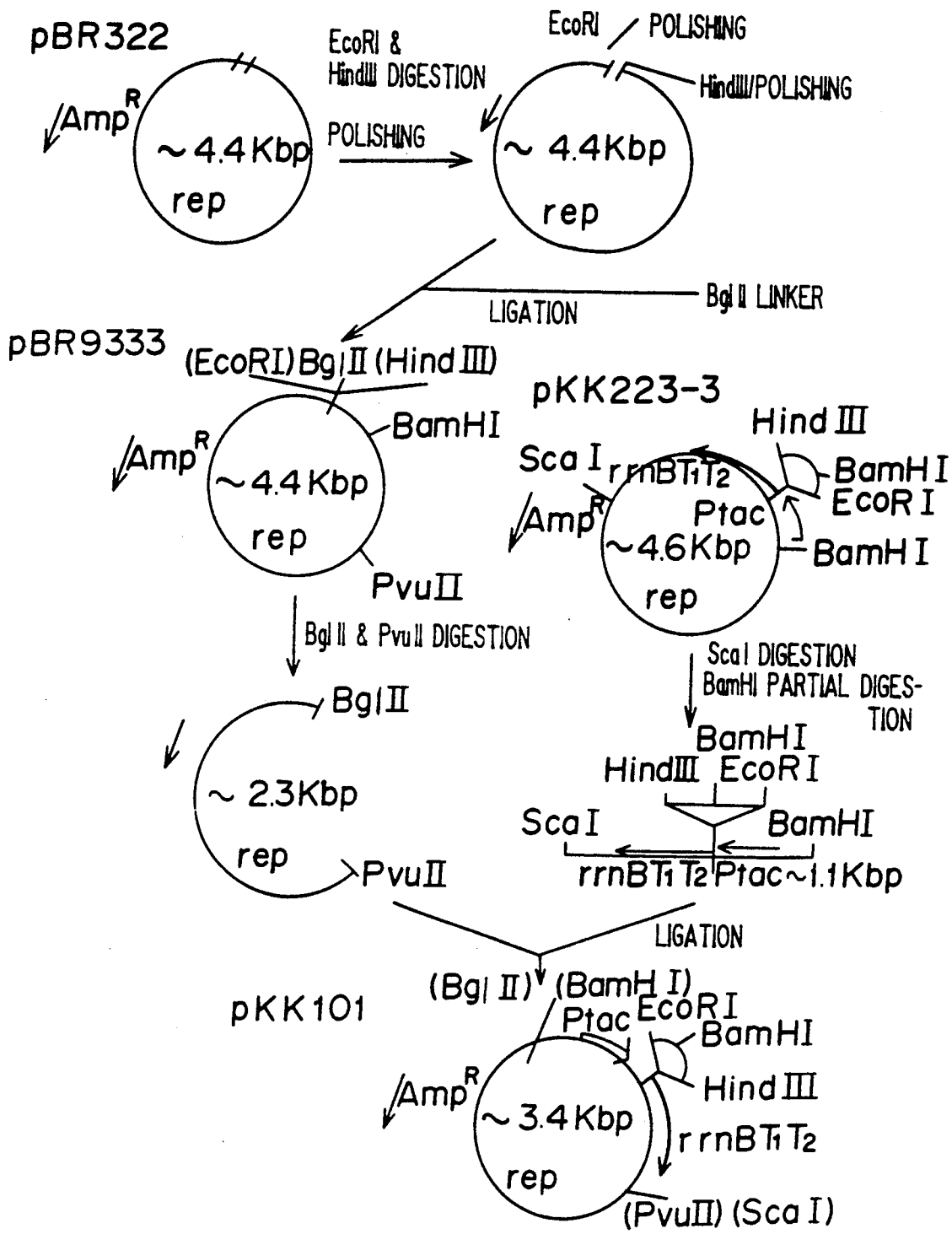
FIG. 3 illustrates the process steps for cloning an expression plasmid vector.

The method is illustrated in FIG. 3.

5 μg of plasmid vector pBR 322 (obtained from Research Laboratory for Genetic Information of Kyushu University) was digested with restriction endonuclease EcoR I and Hind III, in accordance with the method of Example 3, and both termini thereof were polished by means of T4 DNA polymerase. In accordance with the method of Example 3, a DNA fragment of about 4.4 Kbp was separated and purified by agarose gel electrophoresis (gel concentration: 1%). Then, 100 ng of non-phosphorylated Bgl II linker (a double-stranded DNA fragment of 10 bp containing a restriction endonuclease Bgl II cleavage site, obtained from Takara Shuzo, Catalogue No. 4721A, Takara Biotechnology Catalogue 1991 Vol. 1) was inserted and ligated to the ring-opened site thereof by means of T4 DNA ligase. The plasmid contained in the transformant obtained in the same manner as in Example 3 was examined by the digestion with the restriction endonuclease, whereby it was confirmed that a clone having the desired plasmid pBR 9333 (about 4.4 Kbp) having the restriction endonuclease EcoR I and Hind III cleavage sites deleted and having a restriction endonuclease Bgl II cleavage site newly inserted, was obtained.

Then, 5 μg of plasmid pBR 9333 thus obtained, was dissolved in a high salt buffer, in accordance with the method of Example 3, and digested with restriction endonuclease Bgl II (Takara Shuzo) and Pvu II (Takara Shuzo). Then, a DNA fragment of about 2.3 Kbp containing a replication origin was separated and purified by agarose gel electrophoresis (gel concentration: 1%). On the other hand, 5 μg of expression vector pKK 223-3 (about 4.6 Kbp) was dissolved in a high salt buffer in the same manner as above and digested with restriction endonuclease BamH I (Takara Shuzo) and Sca I (Takara Shuzo). The digestion reaction with the restriction endonuclease BamH I was conducted by partial digestion for a reaction time of from 5 to 30 minutes by reducing the amount of the added enzyme to a level of about ½ of a usual amount. After the digestion treatment, the obtained DNA fragment of about 1.1 Kbp containing tac promoter and rrnBT$_1$T$_2$ terminator was separated and purified by agarose gel electrophoresis in the same manner as above. The DNA fragment of about 1.1 Kbp was inserted and ligated to the previously purified DNA fragment of about 2.3 Kbp containing a replication origin, by means of T4 DNA ligase in the same manner as described above. The ligated DNA was introduced into competent cells of an *E. coli* K-12 JM103 strain (obtained from Research Laboratory for Genetic Information of Kyushu University) prepared by a calcium chloride method, in accordance with the method of Example 3. From the transformants thus obtained, a clone having the desired expression vector (about 3.4 Kbp) containing tac promoter was selected, and this expression vector was designated as pKK 101.

Figure 4:
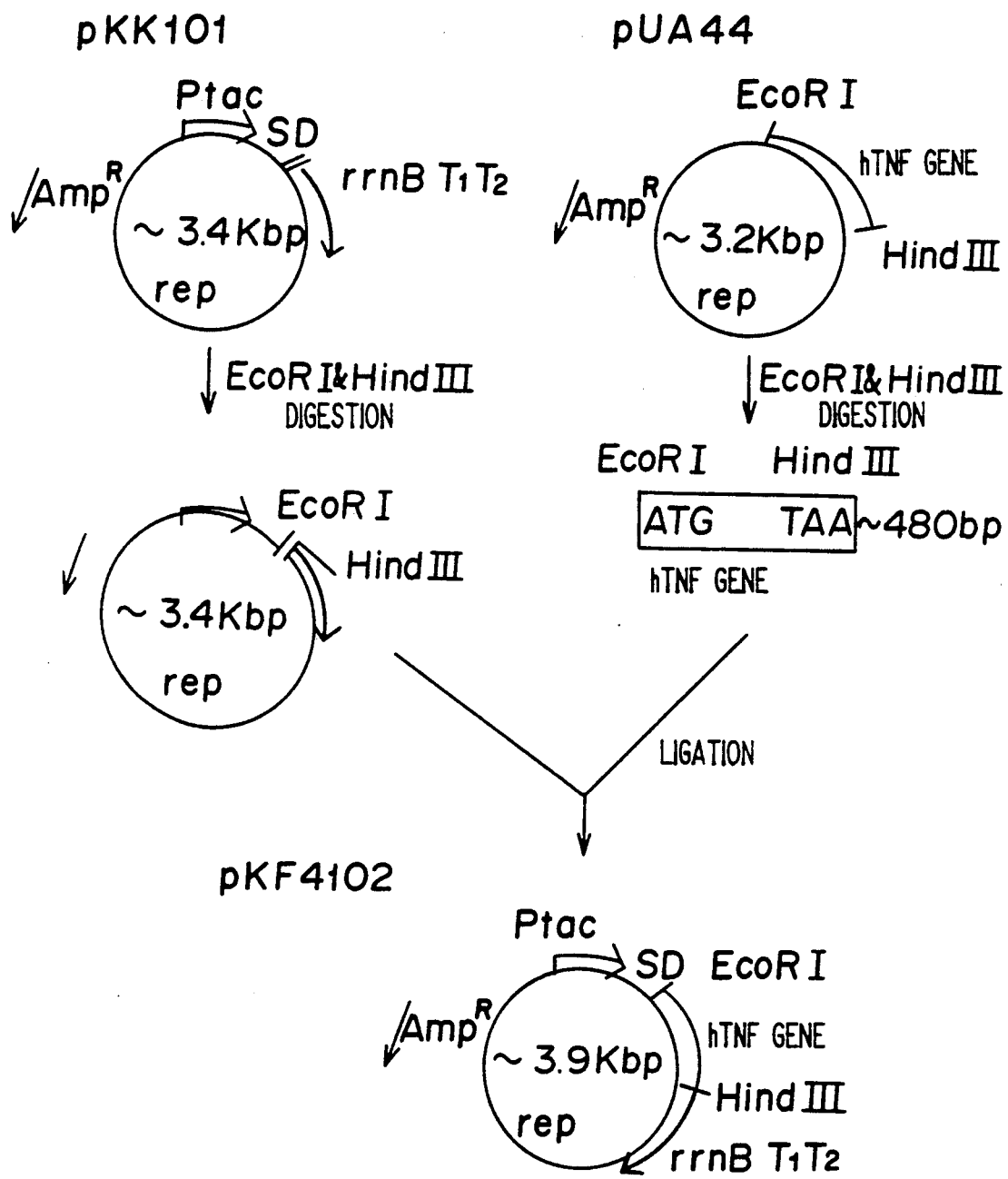
FIG. 4 illustrates the process steps for cloning a human TNF expression vector.

(2) Referring to FIG. 4, the subsequent step will be described.

Five μg of the expression vector pKK 101 obtained in the above step (1) was digested with restriction endonuclease EcoR I and Hind III, in accordance with the above-mentioned method, and a DNA fragment of about 3.4 Kbp containing a replication origin and a transcriptional regulation region, was separated and purified by agarose gel electrophoresis (gel concentration: 1%). Likewise, the plasmid pUA44 (about 3.2 Kbp) containing the human TNF gene obtained in Example 3 was digested with restriction endonuclease EcoR I and Hind III, whereupon a DNA fragment of about 480 bp containing the entire region of a human TNF gene was separated and purified by agarose gel electrophoresis. This DNA fragment containing the entire region of a human TNF gene was inserted and ligated to the DNA fragment of about 3.4 Kbp previously purified from the expression vector pKK 101, by means of T4 DNA ligase in accordance with the above-mentioned method. The ligated DNA was introduced into an *E. coli* K-12 JM103 strain in accordance with the above-mentioned method. From the transformants thus obtained, a clone having the desired human TNF expression vector (about 3.9 Kbp) was selected, and this expression vector was designated as pKF 4102.

EXAMPLE 5

Cloning of plasmid pUC119-F4104

Figure 5:
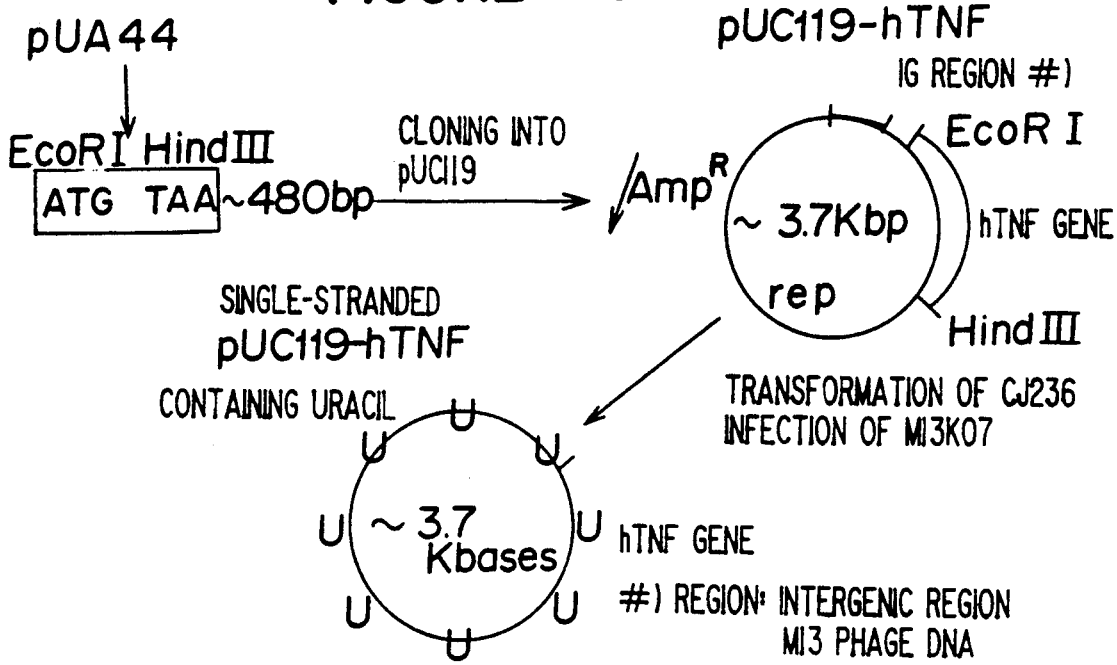
FIG. 5 illustrates the process steps for preparing a human TNF mutein or N-terminal mutein gene by site directed mutagenesis.

(1) The operation will be described with reference to FIG. 5.

The plasmid pUA44 obtained in Example 3 was digested with restriction endonuclease EcoR I and Hind III, in accordance with the above mentioned method, and a DNA fragment of the human TNF gene (about 480 bp containing the entire region) was separated and purified by agarose gel electrophoresis. On the other hand, plasmid vector pUC119 (obtained from Takara Shuzo) for the preparation of a single-stranded plasmid DNA developed by Messing et al. (*Methods in Enzymology*, 153, 3 (1987)) was likewise digested with restriction endonuclease EcoR I and Hind III, and a DNA fragment of about 3.2 Kbp containing an intergenic (IG) region was separated and purified by agaros gel electrophoresis. By the presence of this IG region (intergenic region of M13 phage DNA), the plasmid pUC119 will, after being infected to a helper phage M13K07, preferentially become a single-stranded DNA and will be enclosed by phage particles and will be discharged out of the microbial cells. The DNA fragment of about 480 bp purified as above and containing the entire region of the human TNF gene and the pUC119 fragment of about 3.2 Kbp containing the IG region were ligated by means of T4 DNA ligase in accordance with the above-mentioned method, and the ligated DNA was introduced into an *E. coli* K-12 JM83 strain in accordance with the method of Example 3. From the transformants thus obtained, a clone having the desired plasmid (about 3.7 Kbp) was selected. This clone was designated as pUC119-hTNF/JM83, and the plasmid was designated as pUC119-hTNF.

The plasmid pUC119-hTNF thus obtained was introduced into competent cells of an *E. coli* CJ236 strain (dut$^-$, ung$^-$) prepared by a calcium chloride method, in accordance with the method of Example 3, to incorporate uracil into the DNA of the plasmid. The CJ236 strain has a mutation (dut$^-$) in the enzyme dUTPase (deoxyuridine triphosphate-phosphatase) gene, and a competing reaction is thereby caused, whereby it is possible to produce a DNA having uracil partially incorporated instead of thymine. Further, due to the ung$^-$ mutation, it lacks the enzyme uracil N-glycosylase, whereby it is possible to maintain uracil in the DNA. Such CJ236 strain was obtained from Bio-Rad. The clone (pUC119-hTNF/CJ236) obtained by such introduction was, after infected with helper phage M13K07 (obtained from Takara Shuzo), cultured in a 2×YT broth (1.6% tryptone, 1% yeast extract and 0.5% NaCl pH 7.6) containing 100 μg/ml of ampicillin, 70 μg/ml of Kanamycin and 30 μg/ml of chloramphenicol, whereby the desired single-stranded plasmid DNA (about 3.7 K bases) having uracil introduced was discharged out of the cells in a form enclosed by phage particles. The discharged phage particles were recovered from the supernatant of the broth, and the desired single-stranded plasmid DNA was prepared in accordance with a method for preparing a single-stranded phage DNA.

Figure 6:
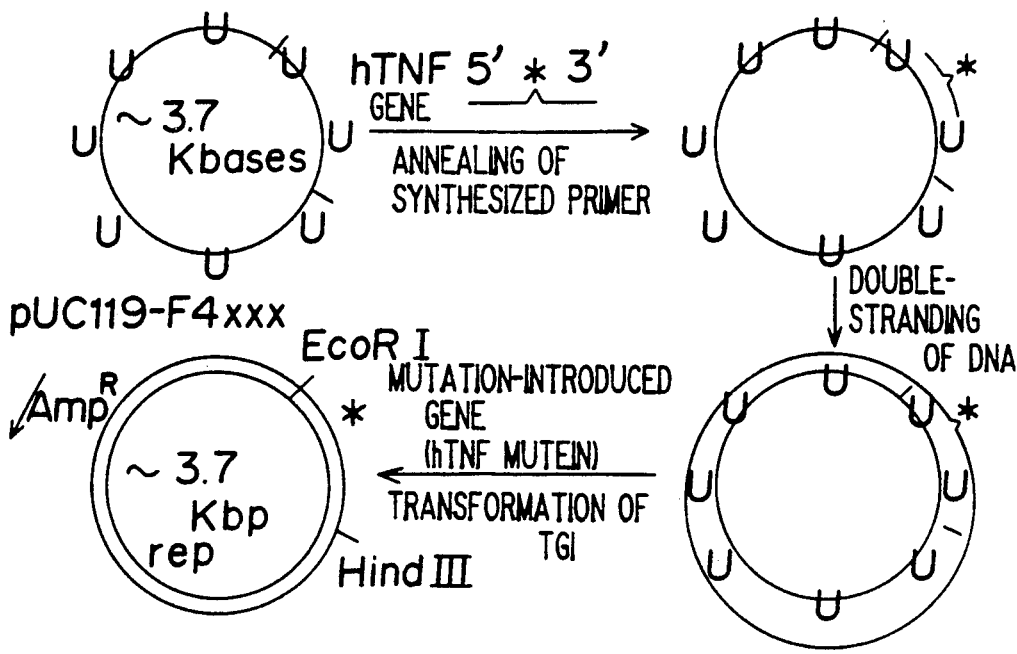
FIG. 6 illustrates the process steps for preparing a human TNF mutein or N-terminal mutein gene by site directed mutagenesis.

(2) The operation will be described with reference to FIG. 6.

Primer 4104 was designed to introduce a mutation to the human TNF gene using a coding strand oligonucleotide.

Primer 4104 is an oligonucleotide comprising 16 bases with a nucleotide sequence of from the 5th C to the 20th G as shown by SEQ ID NO:7 in the Sequence Listing wherein the 13th A is replaced by G.

The chemical synthesis and purification of this oligonucleotide was conducted in accordance with the method of Example 2.

The site-directed mutagenesis of the human TNF gene was conducted in accordance with the Bio-Rad system (Muta-Gene ™ in vitro mutagenesis kit). Namely, about 0.5 μg of the primer prepared as above and having the 5'-terminus phosphorylated with T4 polynucleotide kinase in accordance with the above-mentioned method and about 200 ng of the previously prepared uracil-introduced single-stranded plasmid DNA (pUC119-hTNF) were annealed in 10 μl of an annealing buffer (20 mM Tris-HCl pH 7.4, 2 mM MgCl$_2$ and 50 mM NaCl) (i.e. heated at 70° C. followed by gradual cooling). After completion of the annealing, a 1/10 volume of 10×synthesis buffer (5 mM deoxyribonucleotide triphosphates (dATP, dGTP, dCTP and TTP), 10 mM ATP, 100 mM Tris-HCl pH 7.4, 50 mM MgCl$_2$ and 20 mM DTT) was added thereto, and a double-stranding reaction (37° C., 90 minutes) was conducted by means of 1 unit of T4 DNA polymerase and from 2 to 4 units of T4 DNA ligase. About 8 volumes of TE buffer (10 mM Tris-HCl pH7.5 and 1 mM EDTA) was added and the mixture was freezed to stop the reaction. This reaction mixture was applied to competent cells of the E. coli K-12 TG1 strain (ung+, obtained from Amersham) prepared by a calcium chloride method, in accordance with the method of Example 3, to introduce the double stranded DNA.

By the introduction of the hetero double-stranded DNA into the ung+ strain, the uracil-containing DNA strand as the template was deactivated and not replicated. (Therefore, the mutation frequency becomes as high as more than 50%.) From the transformants thus obtained, a clone having a plasmid (about 3.7 Kbp) containing the desired mutein DNA was selected by means of colony hybridization method employing as a probe the primer used for the introduction of mutation. With respect to the selected clone, the nucleotide sequence around the mutation-introduced site of the plasmid was examined by the dideoxy method (F. Sanger as mentioned above) to confirm that it was modified to the mutein DNA as designed. This plasmid was designated as pUC119-F4104. The mutation of pUC119-F4104 is a substitution of G for the 13th A in the sequence of SEQ ID NO:7 in the Sequence Listing, and as a result, a restriction endonuclease Xho I cleavage site was formed.

EXAMPLE 6

Cloning of human TNF N-terminal mutein expression vector pKF 4146

Figure 7:
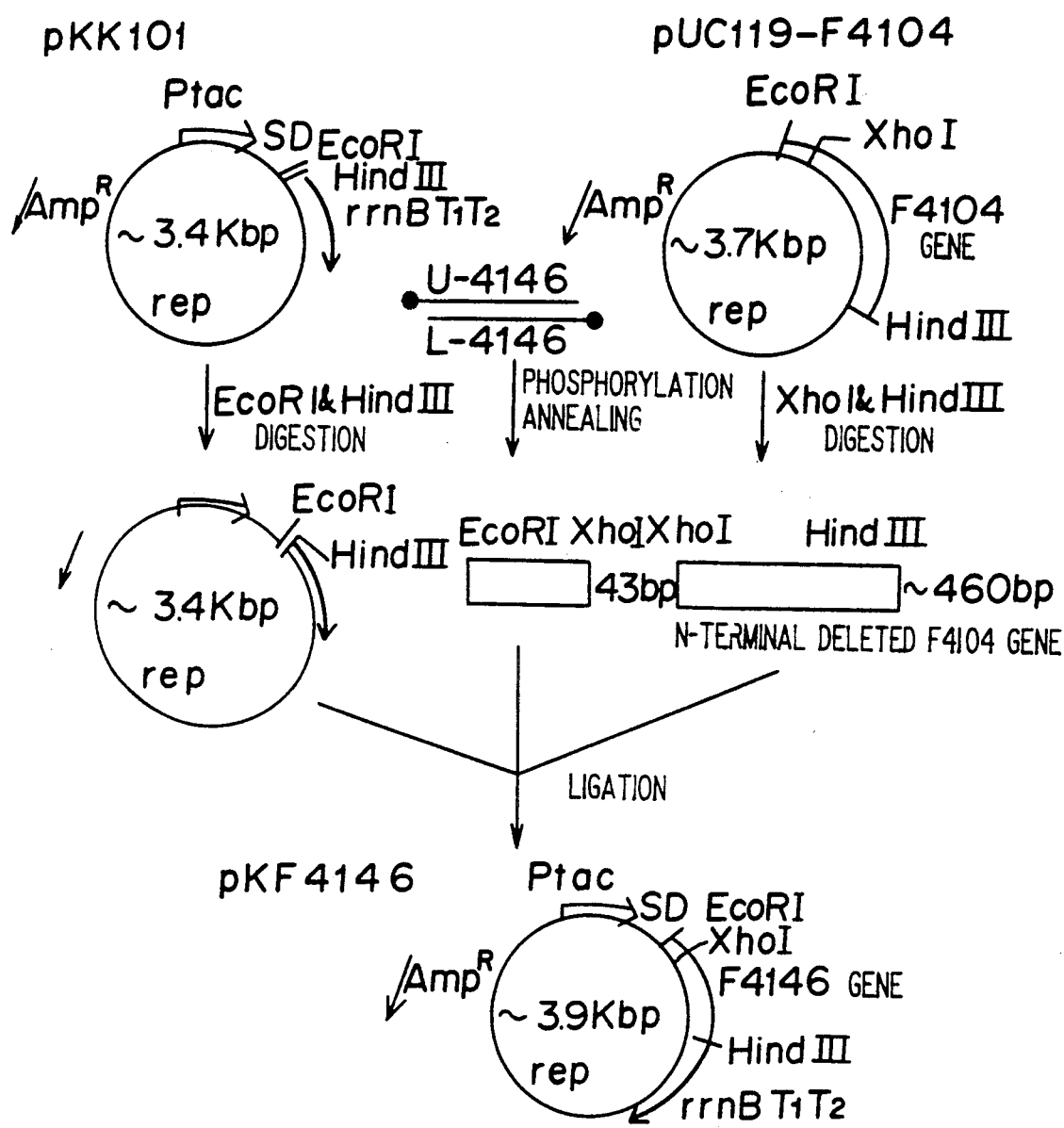
FIG. 7 illustrates the process steps for cloning a human TNF N-terminal mutein expression vector by gene recombination utilizing restriction endonuclease cleavage sites.

Using the plasmid pUC119-F4104 having a restriction endonuclease Xho I cleavage site obtained in Example 5, an expression vector (designated as pKF 4146) of an N-terminal added human TNF N-terminal mutein polypeptide (designated as F4146) was cloned by ligating a chemically synthesized oligonucleotide (double-stranded by annealing) to the N-side of the restriction endonuclease Xho I cleavage site. This cloning method will be described with reference to FIG. 7.

Five μg of plasmid pUC119-F4104 (about 3.7 Kbp) was dissolved in a high salt buffer in accordance with the method of Example 3 and digested with restriction endonuclease Xho I (Takara Shuzo) and Hind III, whereupon a DNA fragment of about 460 bp containing F4104 gene having the N-terminal portion deleted, was separated and purified by agarose gel electrophoresis (gel concentration: 1%). On the other hand, the upper strand (U-4146) and the lower strand (L-4146) of an oligonucleotide encoding an oligopeptide designed for the purpose of addition to the N-terminal portion of F4104, were chemically synthesized and purified in accordance with the method of Example 2. The upper strand U-4146 has the nucleotide sequence as shown by SEQ ID NO:8 in the Sequence Listing. The lower strand L-4146 is complementary to the upper strand, but this lower strand does not have a nucleotide sequence complementary to the 1-4th 5'-AATT-3' of SEQ ID NO:8. On the other hand, it has a nucleotide sequence having 5'-TCGA-3' joined to the 5'-side of G which is complementary to the 43rd C of SEQ ID NO:8. The two oligonucleotides (each 1 μg) obtained after purification were phosphorylated at their 5'-termini with T4 polynucleotide kinase in accordance with the method of Example 3, followed by annealing to obtain a double-stranded DNA fragment (43 bp). On the other hand, the plasmid vector pKK 101 was digested with restriction endonuclease EcoR I and Hind III in accordance with the method of Example 4, whereupon a DNA fragment of about 3.4 Kbp containing a replication origin and a transcription regulation region, was separated and purified.

The three DNA fragments obtained by the above method were ligated with T4 DNA ligase, in accordance with the method of Example 3, and ligated DNA was introduced into competent cells of an E. coli K-12 JM103 strain. From the transformants thus obtained, a clone having the desired F4146 expression vector pKF 4146 (about 3.9 Kbp) was selected by confirming the digestion patterns with restriction endonuclease EcoR I, Xho I and Hind III and by examining the nucleotide sequence around the N-terminal addition site of the N-terminal mutein polypeptide.

The N-terminal mutein expression vector cloned in accordance with the above method, induces the expression to produce a novel physiologically active polypeptide having the following replacement in E. coli cells.

Vector pKF 4146: coding for polypeptide F4146 having the amino acid sequence as shown by SEQ ID NO:1 in the Sequence Listing wherein the 1-8th amino acid sequence is replaced by the amino acid sequence shown by SEQ ID NO:3.

EXAMPLE 7

Cloning of human TNF N-terminal mutein expression vectors pKF 4422 and pKF 4423

Five μg of the human TNF N terminal mutein expression vector pKF 4146 (about 3.9 Kbp) obtained in Example 6 was dissolved in a high salt buffer in accordance with the method of Example 3 and digested with restriction endonuclease Bgl II and Hind III, whereupon a DNA fragment of about 470 bp containing F4146 gene having the N-terminal portion deleted, was separated and purified by agarose gel electrophoresis (gel concentration: 1%). On the other hand, the upper strand (U-4422 or U-4423) and the lower strand (L-4422 or L-4423) of an oligonucleotide encoding an oligopeptide designed for the purpose of addition to the N-terminal portion of F4146 were designed.

U-4422 (SEQ ID NO:9 in the Sequence Listing, number of bases: 21).

L-4422 (number of bases: 21) which is complementary to the upper strand U-4422, but has no nucleotide sequence complementary to the 1-4th 5'-AATT-3' of SEQ ID NO:9, and which has a nucleotide sequence having 5' GATC-3' joined to the 5'-side of T complementary to the 21st A of SEQ ID NO:9.

U-4423 (SEQ ID NO:10 in the Sequence Listing, number of bases:36).

L-4423 (number of bases:36) which is complementary to the upper strand U-4423, but has no nucleotide sequence complementary to the 1-4th 5'-AATT-3' of SEQ ID NO:10, and which has a nucleotide sequence having 5'-GATC-3'joined to the 5'-side of T complementary to the 36th A of SEQ ID NO:10.

These oligonucleotides were chemically synthesized and purified in accordance with the method of Example 2. The respective upper and lower oligonucleotides (each 1 µg) obtained after the purification, were phosphorylated at their 5'-termini with T4 polynucleotide kinase in accordance with the method of Example 3, followed by annealing to obtain a double-stranded DNA fragment (21bp or 36bp).

On the other hand, plasmid vector pKK 101 was digested with restriction endonuclease EcoR I and Hind III in accordance with the method of Example 4, and a DNA fragment of about 3.4 Kbp containing a replication origin and a transcriptional regulation region was separated and purified. The three DNA fragments obtained by the above method were ligated by means of T4 DNA ligase, in accordance with the method of Example 3, and the ligated DNA was introduced into competent cells of an E. coli K-12 JM103 strain. From the transformants thus obtained, a clone having the desired F4422 expression vector pKF 4422 (about 3.9 Kbp) or F4423 expression vector pKF 4423 (about 3.9 Kbp) was selected by confirming the digestion patterns with restriction endonuclease EcoR I, Bgl II and Hind III and by examining the nucleotide sequence around the N-terminal addition site of the N-terminal mutein polypeptide.

The N-terminal mutein expression vector thus cloned by the above method induces the expression to produce a novel physiologically active polypeptide having the following replacement in E. coli cells.

Vector pKF 4422: coding for polypeptide F4422 having [. the amino acid sequence as shown by SEQ ID NO:1 in the Sequence Listing wherein the 1–8th amino acid sequence is replaced by the amino acid sequence shown by SEQ ID NO:5.

Vector pKF 4423: coding for polypeptide F4423 having the amino acid sequence as shown by SEQ ID NO:1 in the Sequence Listing wherein the 1–8th amino acid sequence is replaced by the amino acid sequence shown by SEQ ID NO:6.

EXAMPLE 8

Cloning of human TNF N-terminal mutein expression vector pKF 4236

(1) A method for cloning an expression vector having trp promoter will be described with reference to FIGS. 8 to 11.

Figure 8:
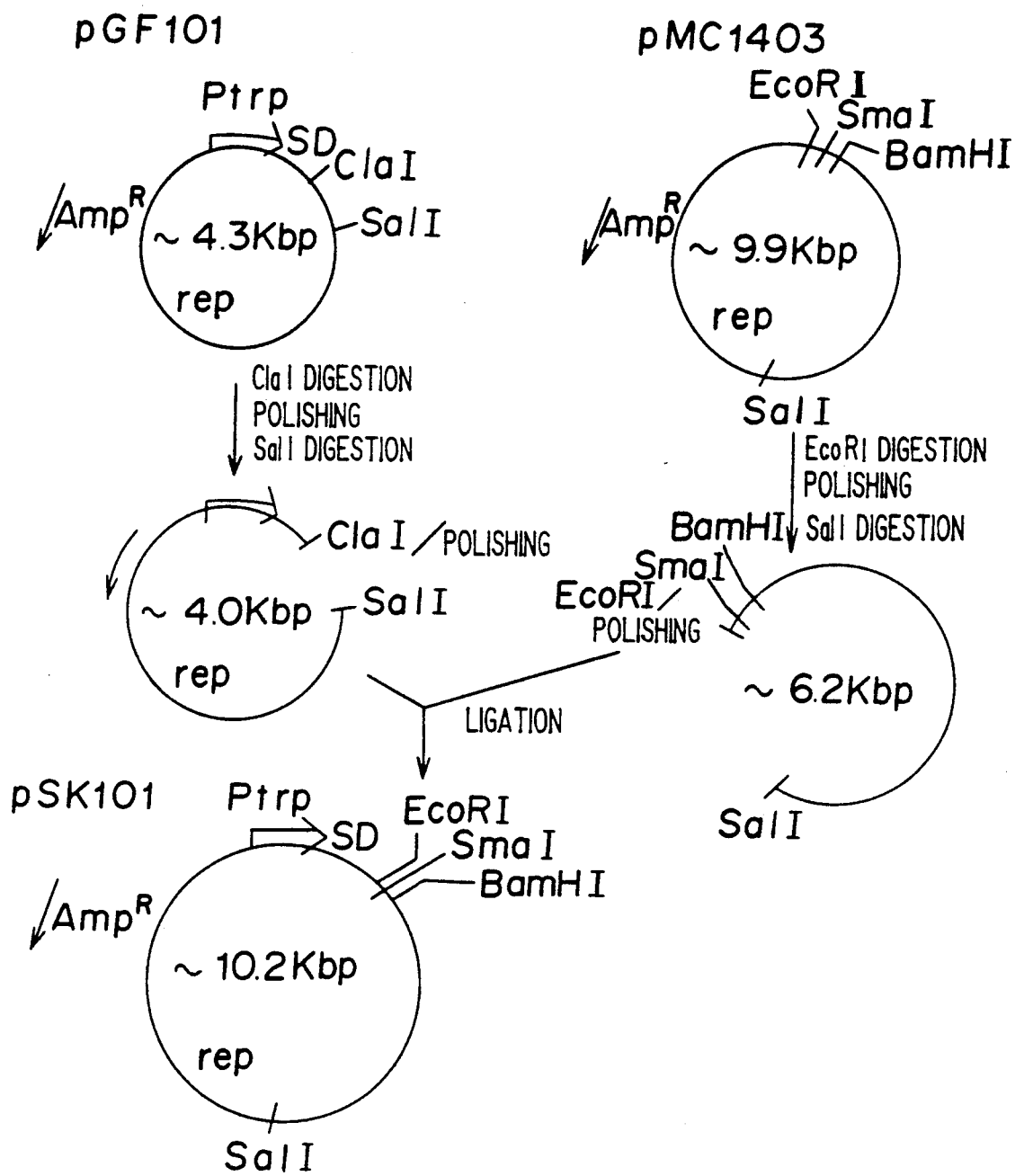
FIG. 8 illustrates the process steps for cloning an expression plasmid vector.
Figure 9:
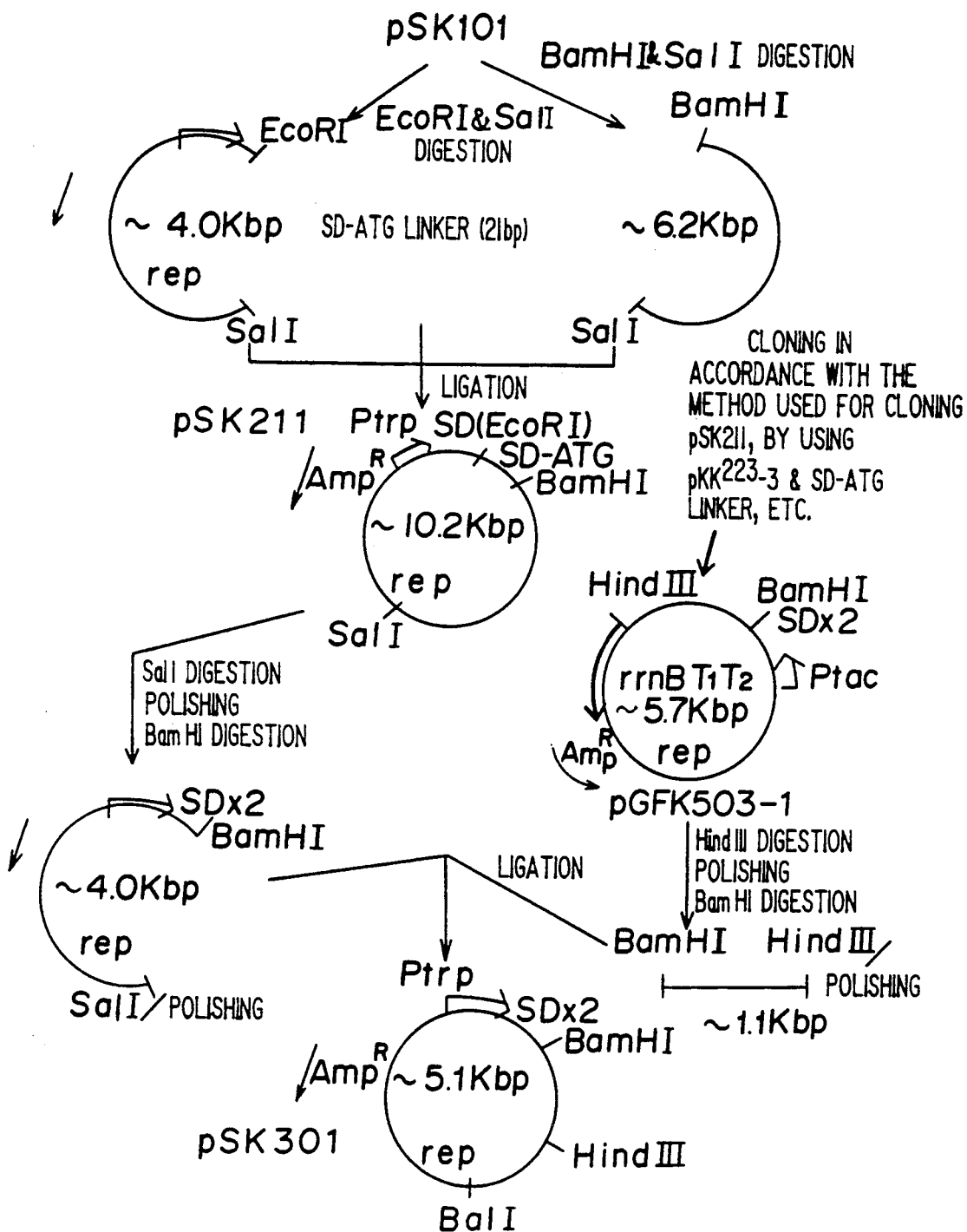
FIG. 9 illustrates the process steps for cloning an expression plasmid vector.
Figure 10:
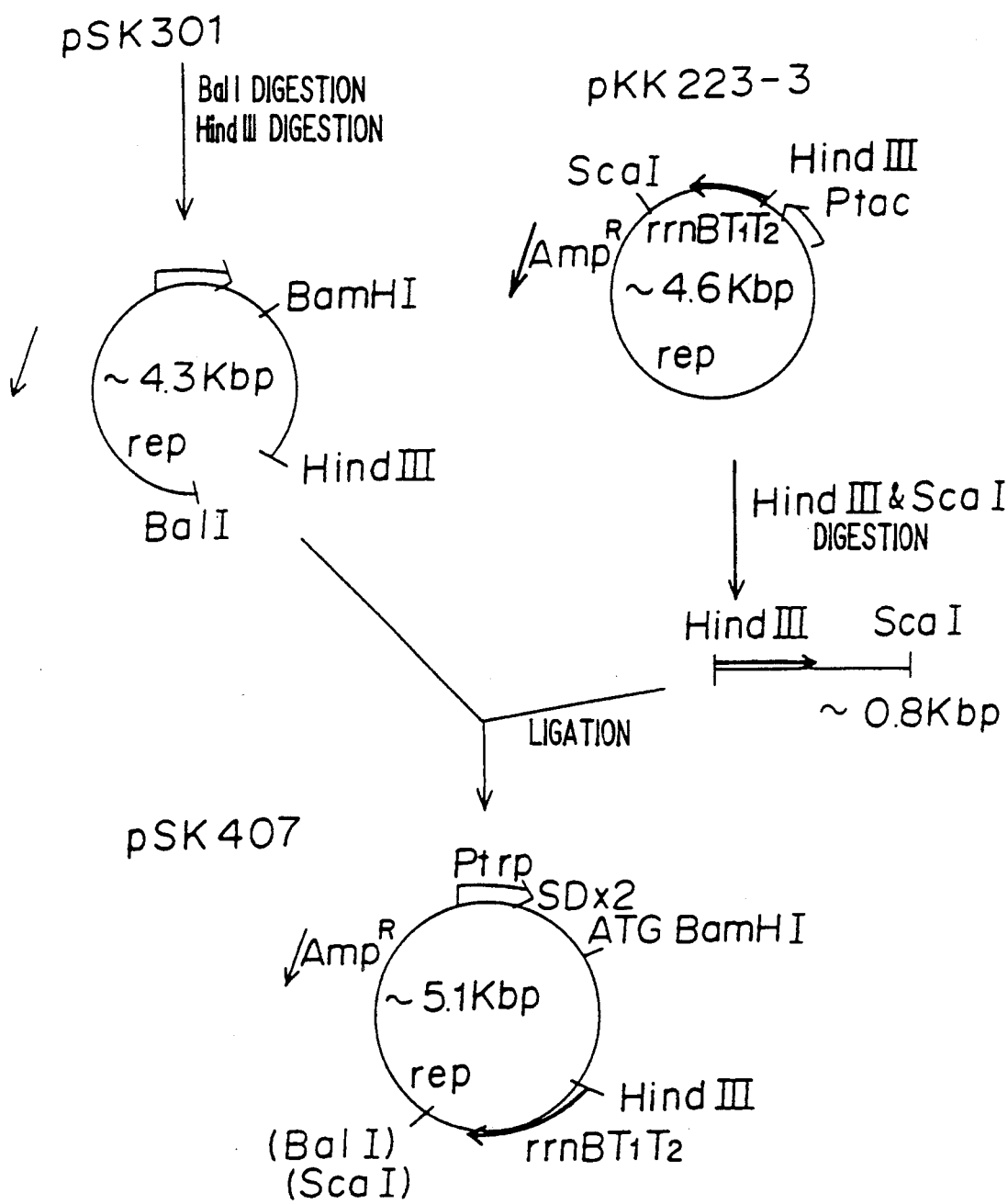
FIG. 10 illustrates the process steps for cloning an expression plasmid vector.

A plasmid vector (designated as pSK407) having trp promoter as the promoter, two translation initiation signals (SD sequence) arranged in tandem and rrnBT$_1$T$_2$ terminator as the terminator, was cloned in accordance with the method shown in FIGS. 8 to 10. Five µg of plasmid vector pGF101 (about 4.3 Kbp, obtained from Facalty of Pharmaceutical Science, Osaka University) was dissolved in a medium salt buffer in accordance with the above-mentioned method and digested by an addition of 10 units of restriction endonuclease Cla I (Takara Shuzo). The cut DNA fragment was polished by means of T4 DNA polymerase in accordance with the method of Example 3, and after the ethanol precipitation operation, it was dissolved in a high salt buffer having NaCl added to a NaCl concentration of 175 mM and digested by an addition of 15 units of restriction endonuclease Sal I (Takara Shuzo). A DNA fragment of about 4.0 Kbp was separated and purified by agarose gel electrophoresis (gel concentration: 1%) in accordance with the method of Example 3.

On the other hand, 5 µg of plasmid pMC1403 (about 9.9 Kbp, obtained from Institute for Virus Research, Kyoto University) developed by Casadaban et al. (J. Bacteriol., 143, 971 (1980)), was digested with restriction endonuclease EcoR I in accordance with the above-mentioned method, followed by polishing and digestion with restriction endonuclease Sal I in the same manner as above, whereupon a DNA fragment of about 6.2 Kbp was separated and purified by agarose gel electrophoresis. In accordance with the method of Example 3, this DNA fragment was ligated to the previously purified DNA fragment by means of T4 DNA ligase, and the ligated DNA was introduced into competent cells of an E. coli K-12 HB101 strain (obtained from Institute for Virus Research, Kyoto University) prepared by a calcium chloride method. From the transformants thereby obtained, a clone having the desired plasmid vector (designated as pSK101) of about 10.2 Kbp containing trp promoter and restriction endonuclease EcoR I and BamH I cleavage sites, was selected.

In each of two tubes, 5 µg of the plasmid vector pSK101 obtained above was dissolved in a high salt buffer in accordance with the above-mentioned method and digested by an addition of restriction endonuclease EcoR I and Sal I, and restriction endonuclease BamH I and Sal I, respectively, whereupon DNA fragments of about 4.0 Kbp and about 6.2 Kbp were, respectively, separated and purified by agarose gel electrophoresis. On the other hand, the upper and lower strands (each 100 ng) of a portable translation initiation site-oligonucleotide (which is referred to simply as SD-ATG linker and which is an oligonucleotide comprising 21 bases containing a translation initiation signal SD sequence and a translation initiation codon ATG, obtained from Pharmacia, Catalogue No. 27-4878-01 and 27-4898-01 Pharmacia Molecular Biologicals, 1985 May) were phosphorylated at their 5'-termini and annealed to obtain a double stranded DNA fragment (21 bp).

The three DNA fragments obtained above were ligated by means of T4 DNA ligase, in accordance with the above-mentioned method, and the ligated DNA was introduced into competent cells of an E. coli K-12 HB101 strain. From the transformants thereby obtained, a clone having the desired plasmid vector (designated as pSK211) of about 0.2 Kbp having the SD-ATG linker inserted downstream of the trp promoter and immediately before the restriction endonuclease BamH I cleavage site, was selected. This plasmid vector has two SD sequences arranged in tandem downstream of the trp promoter. The following operation was conducted for the purpose of eliminating the restriction endonuclease Sal I cleavage site of this plasmid vector and introducing a new restriction endonuclease Hind III cleavage site in its vicinity. Five µg of plasmid vector pSK211 was digested with restriction endonuclease Sal I in accordance with the above-mentioned method and then polished by means of T4 DNA polymerase. The DNA fragment recovered by an ethanol precipitation operation was digested with restriction endonuclease BamH I, whereupon a DNA fragment of about 4.0 Kbp was separated and purified by agarose gel electrophoresis. On the other hand, 5 μg of plasmid vector pGFK 503-1 (about 5.7 Kbp) cloned by recombination in the same manner as the above-mentioned cloning of pSK211, using plasmid vector pKK 223-3 having tac promoter and SD-ATG linker, etc., was digested with restriction endonuclease Hind III in accordance with the above-mentioned method and then polished by means of T4 DNA polymerase. The DNA fragment recovered by an ethanol precipitation operation, was digested with restriction endonuclease BamH I, and a DNA fragment of about 1.1 Kbp was separated and purified by agarose gel electrophoresis.

The two DNA fragments purified above, were ligated by means of T4 DNA ligase, in accordance with the above-mentioned method, and the ligated DNA was introduced into competent cells of an E. coli K-12 HB101 strain. From the transformants thereby obtained, a clone having the desired plasmid vector (designated as pSK301) of about 5.1 Kbp containing trp promoter having the restriction endonuclease Sal I cleavage site deleted and having a Hind III cleavage site formed anew, was selected.

Five μg of this plasmid vector pSK301 was dissolved in a low salt buffer in accordance with the above-mentioned method, and the digestion reaction was conducted by an addition of 5 units of restriction endonuclease Bal I (Takara Shuzo). After completion of the reaction, the NaCl concentration was adjusted to 50 mM, and digestion with restriction endonuclease Hind III was conducted, whereupon a DNA segment of about 4.3 Kbp was separated and purified by agarose gel electrophoresis. On the other hand, 5 μg of plasmid vector pKK 223-3 was dissolved in a high salt buffer in accordance with the above-mentioned method and digested with restriction endonuclease Hind III and Sca I, whereupon a DNA fragment of about 0.8 Kbp was separated and purified by agarose gel electrophoresis.

The two DNA fragments purified above, were ligated by means of T4 DNA ligase, in accordance with the above-mentioned method, and the ligated DNA was introduced into competent cells of an E. coli K-12 HB101 strain. From the transformants thereby obtained, a clone having the desired plasmid vector pSK407 (about 5.1 Kbp) having the rrnBT$_1$T$_2$ terminator located downstream of the trp promoter, was selected.

Then, a TNF mutein expression vector under control of the transcription and translation signal by the plasmid vector pSK407 obtained by cloning in accordance with the above method, was designed. The mutein polypeptide (designated as F4113) to be coded, is a polypeptide having an oligopeptide Asp-Pro-Gly-Arg-Gly-Asp-Ser-Pro added to the N-terminus of human TNF and having the 5th Thr changed to Ala. Two oligonucleotides (U-4113 and L-4113) were designed in accordance with the amino acid sequence of the oligopeptide to be added.

U-4113 (SEQ ID NO:11 in the Sequence Listing, number of bases: 32)

L-4113 (number of bases: 32) which is complementary to U-4113, but does not have a nucleotide sequence complementary to the 1–4th 5'-GATC-3' of SEQ ID NO:11, and on the other hand, has a nucleotide sequence having 5'-TCGA-3' joined to the 5'-side of G complementary to the 32nd C of SEQ ID NO:11.

Figure 11:
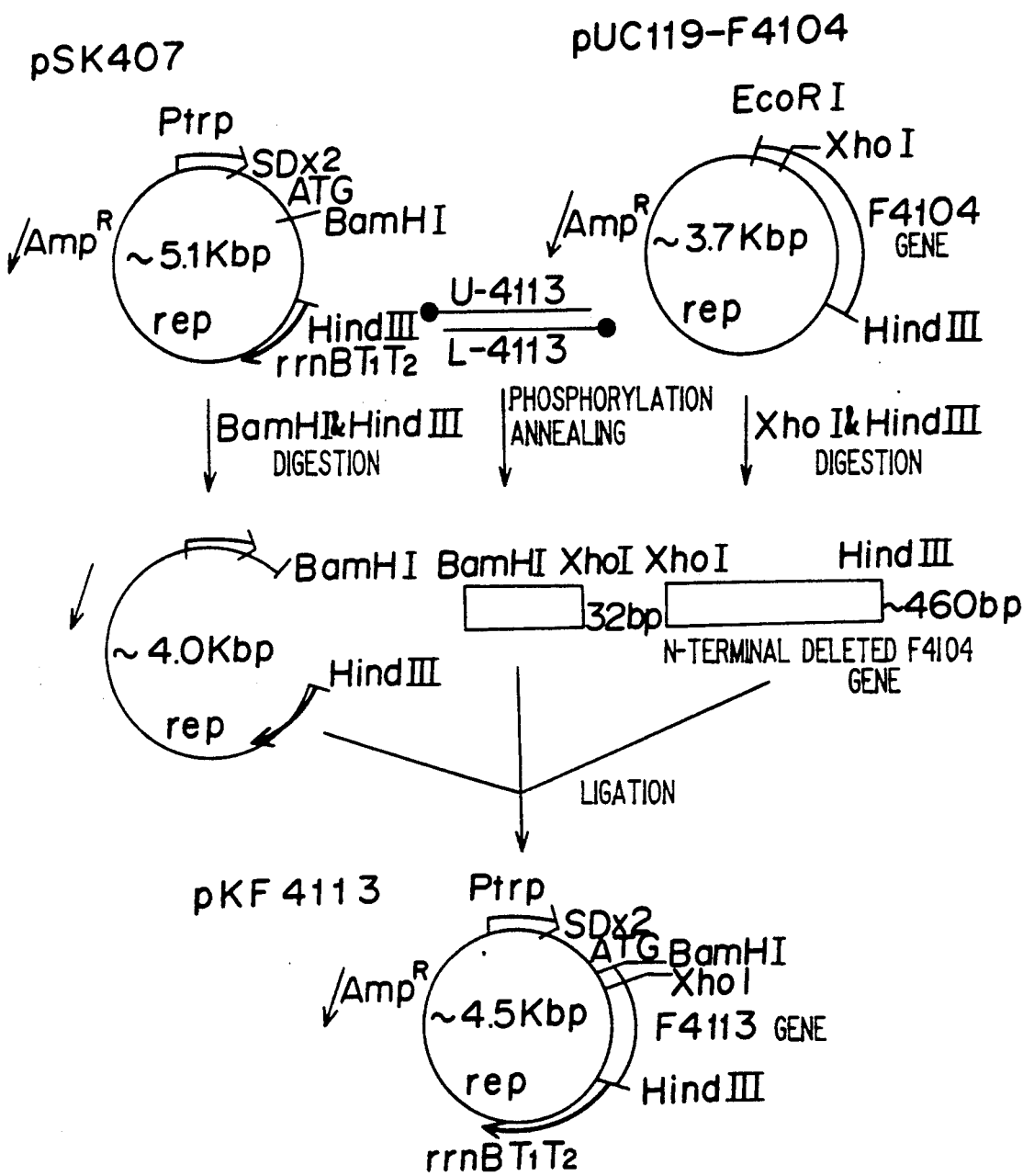
FIG. 11 illustrates the process steps for cloning an expression plasmid vector.

The oligonucleotides (1 μg each) obtained by the chemical synthesis and purification in accordance with the method of Example 2 were phosphorylated at their 5'-termini by means of T4 polynucleotide kinase, followed by annealing, in accordance with the method of Example 3, to obtain a double stranded DNA fragment (32 bp). On the other hand, 5 μg of plasmid vector pSK407 (about 5.1 Kbp) having trp promoter and rrnBT$_1$T$_2$ terminater, etc., was dissolved in a high salt buffer in accordance with the method of Example 3 and digested with restriction endonuclease BamH I and Hind III, whereupon a DNA fragment of about 4.0 Kbp containing a replication origin and a transcriptional regulation region, etc. was separated and purified by agarose gel electrophoresis (gel concentration: 1%). On the other hand, 5 μg of plasmid pUC119-F4104 (about 3.7 Kbp) obtained in Example 5, was digested with restriction endonuclease Xho I and Hind III in the same manner as in Example 6, whereupon a DNA fragment of about 460 bp containing a F4104 gene having the N-terminal portion deleted, was separated and purified (FIG. 11).

The three DNA fragments obtained in accordance with the above methods, were ligated by means of T4 DNA ligase in accordance with the method of Example 3, and the ligated DNA was introduced into competent cells of an E. coli K-12 HB101 strain. From the transformant thereby obtained, a clone having the desired F4113 expression vector (designated as pKF 4113) of about 4.5 Kbp, was selected by confirming the digestion patterns with restriction endonuclease BamH I, Xho I and Hind III and by examining the nucleotide sequence around the N-terminal addition site of the mutein polypeptide.

Figure 12:
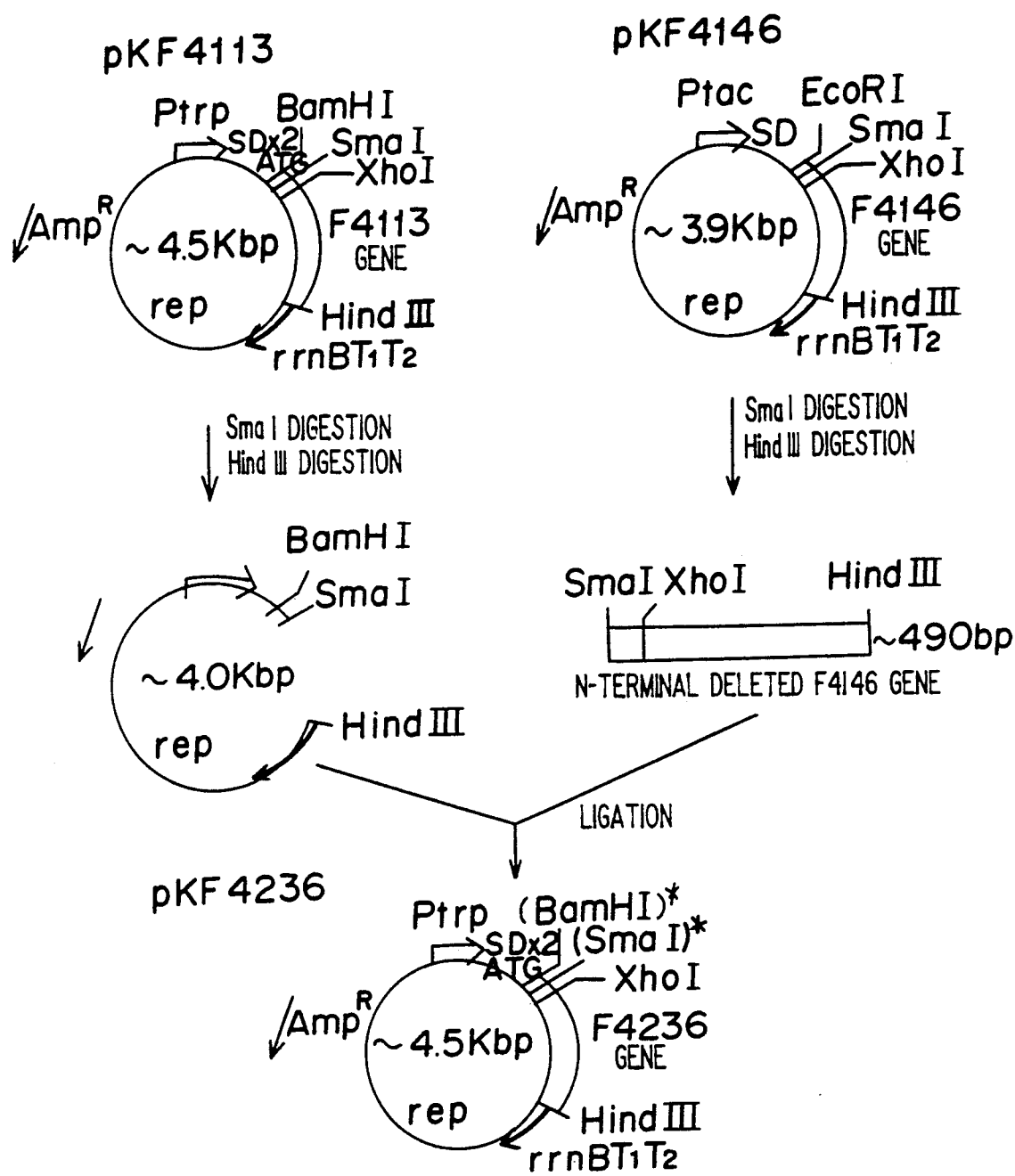
FIG. 12 illustrates the process steps for cloning a human TNF N-terminal mutein expression vector by gene recombination utilizing restriction endonuclease cleavage sites.

(2) The transcription promoter (tac promoter) of the expression vector pKF 4146 obtained in Example 6 is substituted by trp promoter contained in the expression vector pKF 4113 cloned in the above step (1). This substitution also involves a replacement of the N-terminal amino acid sequence. This substitution method will be described with reference to FIG. 12.

Five μg of plasmid pKF 4146 (about 3.9 Kbp) was dissolved in 50 μl of a Sma I buffer (10 mM Tris-HCl pH8.0, 20 mM KCl and 10 mM MgCl$_2$) containing 1 mM of DTT and 100 μg/ml of BSA, and a digestion reaction was conducted at 37° C. for two hours with an addition of 15 units of restriction endonuclease Sma I (Takara Shuzo). After completion of the reaction, a DNA fragment was recovered by an ethanol precipitation operation and again dissolved in 50 μl of a medium salt buffer. A digestion reaction was conducted at 37° C. for two hours with an addition of 15 units of restriction endonuclease Hind III, and then a DNA fragment of about 490 bp was separated and purified by agarose gel electrophoresis (gel concentration: 1%). On the other hand, 5 μg of the plasmid pKF 4113 having trp promoter obtained by cloning in the above step (1) was digested with restriction endonuclease Sma I and Hind III in the same manner as above, and a DNA fragment of about 4.0 Kbp containing trp promoter was separated and purified by agarose gel electrophoresis (gel concentration: 1%).

The two DNA fragments thus obtained were ligated with T4 DNA ligase, in accordance with the method of Example 3, and the ligated DNA was introduced into competent cells of an E. coli K-12 HB101 strain. From the transformant thus obtained, a clone having the desired N-terminal mutein polypeptide expression vector (about 4.5 Kbp) having trp promoter, was selected by confirming the digestion patterns with restriction endonuclease and by examining the nucleotide sequence around the N-terminal addition site of the N-terminal mutein polypeptide. By this selection, a clone which does not reproduce restriction endonuclease Sma I which should be reproduced, was obtained, since it lacks three base pairs coding for Pro:

5'-CCC-3'

3'-GGG-5' this expression vector was designated as pKF 4236.

The N-terminal mutein expression vector cloned in accordance with the above method, induces the expression to produce a novel physiologically active polypeptide having the following replacement in E. coli cells.

Vector pKF 4236: coding for polypeptide F4236 having the amino acid sequence as shown by SEQ ID NO:1 wherein the 1-8th amino acid sequence is replaced by the amino acid sequence shown by SEQ ID NO:2.

EXAMPLE 9

Cloning of human TNF N-terminal mutein expression vector pKF 4419

Using primer 4419 shown by SEQ ID NO:12 in the Sequence Listing, a plasmid (about 3.7 Kbp) containing the desired mutational DNA was prepared in accordance with the method of Example 5 (1) and (2). It was confirmed by the dideoxy method that the DNA was modified to the N-terminal mutein DNA as designed, and this plasmid was designated as pUC119-F4419.

The desired human TNF N-terminal mutein gene obtained by the introduction of mutation, was inserted into expression vector pKK101 having tac promoter in accordance with the method for cloning a human TNF expression vector of Example 4, to obtain a human TNF N-terminal mutein expression vector. The human TNF N-terminal mutein gene (about 480 bp) was separated and purified from the plasmid pUC119-F4419 (about 3.7 Kbp) obtained above, after the digestion with restriction endonuclease EcoR I and Hind III in accordance with the above-mentioned method. The desired human TNF N-terminal mutein expression vector (pKF 4419) was obtained by using as the host an E. coli K-12 JM103 strain in the same manner as in the case of the human TNF expression vector (pKF 4102). The N-terminal mutein expression vector cloned in accordance with the above method induces the expression to produce a novel physiologically active polypeptide having the following replacement in E. coli cells.

Vector pKF 4419: coding for polypeptide F4419 having the amino acid sequence as shown by SEQ ID NO:1 in the Sequence Listing wherein the 1-8th amino acid sequence is replaced by the amino acid sequence shown by SEQ ID NO:4.

EXAMPLE 10

Cloning of human TNF N-terminal mutein expression vectors pKF 4603 and pKF 4604

(1) Primers 4291 and 4292 were designed. These primers are oligonucleotides comprising 21 bases having a nucleotide sequence of from the 193th C to the 213th T of SEQ ID NO:7 wherein the 202-204th 5'-CCA-3' is replaced by 5'-GAT-3' in the case of primer 4291 and by 5'-ATG-3'in the case of primer 4292.

The chemical synthesis and purification of these oligonucleotides were conducted in accordance with the method of Example 2. Using such primer 4291 or 4292, a plasmid (about 3.7 Kbp) containing the desired mutant DNA was obtained in accordance with the method of Example 5 (1) and (2). It was confirmed by the dideoxy method that the DNA was modified to the mutein DNA as designed, and this plasmid was designated as pUC119-F4291 or pUC119-F4292. The desired human TNF mutein gene obtained by the introduction of mutation, was inserted into expression vector pKK 101 having tac promoter in accordance with the method of cloning a human TNF expression vector of Example 4, to obtain a human TNF mutein expression vector. The human TNF mutein gene (about 480 bp) was separated and purified after digestion of the plasmid pUC119-F4291 or pUC119-F4292 (about 3.7 Kbp) obtained above with restriction endonuclease EcoR I and Hind III in accordance with the above-mentioned method. The desired human TNF mutein expression vector pKF 4291 or pKF 4292 (about 3.9 Kbp) was obtained by using as the host an E. coli K-12 JM103 strain in the same manner as in the case of the human TNF expression vector (pKF 102). (2) Five μg of the human TNF N-terminal mutein expression vector pKF 4236 (about 4.5 Kbp) obtained in Example 8 was dissolved in a medium salt buffer, in accordance with the method of Example 3, and digested with restriction endonuclease Sac I and Hind III, whereupon a DNA fragment of about 4.1 Kbp containing a replication origin and a transcriptional regulation region, was separated and purified by agarose gel electrophoresis (gel concentration: 1%). On the other hand, 5 μg of the human TNF mutein expression vector pKF 4291 or pKF 4292 obtained in the above step (1) was digested with restriction endonuclease Sac I and Hind III in the same manner as above, whereupon a DNA fragment of about 360 bp containing a human TNF mutein gene having the N-terminal portion deleted, was separated and purified.

The two DNA fragments obtained by the above methods, were ligated by means of T4 DNA ligase, in accordance with the method of Example 3, and the ligated DNA was introduced into competent cells of an E. coli K-12 HB101 strain. From the transformants thus-obtained, a clone having the desired expression vector pKF 4603 or pKF 4604 (about 4.5 Kbp) for F4603 or F4604 was selected by confirming the digestion pattern with restriction endonuclease Sac I and Hind III and by examining the nucleotide sequence around the replaced sites derived from the mutein polypeptide.

The N-terminal mutein expression vector cloned in accordance with the above method, induces the expression of a novel physiologically active polypeptide having the following replacements in E. coli cells.

Vector pKF 4603: coding for polypeptide F4603 having the amino acid sequence as shown by SEQ ID NO:1 wherein the 1-8th amino acid sequence is replaced by the amino acid sequence shown by SEQ ID NO:2, and the 68th Pro is replaced by Asp.

Vector pKF 4604: coding for polypeptide F4604 having the amino acid sequence as shown by SEQ ID NO:1 wherein the 1-8th amino acid sequence is replaced by the amino acid sequence shown by SEQ ID NO:2, and the 68th Pro is replaced by Met.

Host E. coli cells having the above expression vectors produce polypeptides showing antitumor activities. This was confirmed by a test in which a supernatant fraction obtained after the centrifugal separation of a suspension of sonicated E. coli cells, was tested in accordance with the method of Example 15 given hereinafter.

EXAMPLE 11

Cloning of human TNF N-terminal mutein expression vectors pKF 4616, pKF 4617, pKF 4630, pKF 4631, pKF 4636, pKF 4637, pKF 4618, pKF 4619, pKF 4632, pKF 4633, pKF 4640 and pKF 4641

(1) Primers 4268, 4150, 4222, 4267, 4123 and 4223 were designed. Primer 4268 is an oligonucleotide comprising 30 bases having a nucleotide sequence of from the 301st A to the 333rd C of SEQ ID NO:7 wherein the 316-318th 5'-GGC-3' is deleted. On the other hand, other primers are oligonucleotides having 21 bases having a nucleotide sequence of from the 307th A to 327th C of SEC ID NO: 7 wherein the 316-318th 5'-GGC-3' is replaced by 5'-TGG-3' in the case of primer 4150, by 5'-CCC-3' in the case of primer 4222, by 5'-GCT-3' in the case of primer 4267, by 5'-GAC-3' in the case of primer 4123 and by 5'-CGC-3' in the case of primer 4223.

The chemical synthesis and purification of these oligonucleotides were conducted in accordance with the method of Example 2. Using each of these primers, a plasmid (about 3.7 Kbp) containing the desired mutant DNA was obtained in accordance with the method of Example 5 (1) and (2). It was confirmed by the dideoxy method that the DNA was modified to the mutein DNA as designed, and this plasmid was designated as pUC119-F4268, pUC119-F4150, pUC119-F4222, pUC119-F4267, pUC119-F4123 or pUC119-F4223. The desired human TNF mutein gene obtained by the introduction of mutation, was inserted into expression vector pKK 101 having tac promoter in accordance with the method of cloning a human TNF expression vector of Example 4, to obtain a human TNF mutein expression vector. The human TNF mutein gene (about 480 bp) was separated and purified after digestion of the plasmid (about 3.7 Kbp) obtained above with restriction endonuclease EcoR I and Hind III in accordance with the above-mentioned method. The desired human TNF mutein expression vector pKF 4268, pKF 4150, pKF 4222, pKF 4267, pKF 4123 or pKF 4223 (about 3.9 Kbp) was obtained by using as the host an $E.\ coli$ K-12 JM103 strain in the same manner as in the case of the human TNF expression vector (pKF 4102).

(2) In accordance with the method of Example 10 (2), 5 $\mu$g of the human TNF N-terminal mutein expression vector pKF 4236 (about 4.5 Kbp) obtained in Example 8 was digested with restriction endonuclease Sac I and Hind III, whereupon a DNA fragment of about 4.1 Kbp containing a replication origin and a transcriptional regulation region, was separated and purified.

On the other hand, 5 $\mu$g of the human TNF mutein expression vector pKF 4268, pKF 4150, pKF 4222, pKF 4267, pKF 4123 or pKF 4223 obtained in the above step (1) was digested with restriction endonuclease Sac I and Hind III in the same manner as above, whereupon a DNA fragment of about 360 bp containing a human TNF mutein gene having the N-terminal portion deleted, was separated and purified.

The two DNA fragments obtained by the above methods, were ligated by means of T4 DNA ligase, in accordance with the method of Example 3, and the ligated DNA was introduced into competent cells of an $E.\ coli$ K-12 HB101 strain. From the transformants thus-obtained, a clone having the desired expression vector pKF 4616, pKF 4617, pKF 4630, pKF 4631, pKF 4636 or pKF 4637 (about 4.5 Kbp) for F4616, F4617, F4630, F4631, F4636 or F4637 was selected by confirming the digestion pattern with restriction endonuclease Sac I and Hind III and by examining the nucleotide sequence around the replaced sites derived from the mutein polypeptide.

The N-terminal mutein expression vector cloned in accordance with the above method, induces the expression of a novel physiologically active polypeptide having the following replacements in $E.\ coli$ cells.

Vector pKF 4616: coding for polypeptide F4616 having the amino acid sequence as shown by SEQ ID NO:1 wherein the 1-8th amino acid sequence is replaced by the amino acid sequence shown by SEQ ID NO:2, and the 106th Gly is deleted.

Vector pKF 4617: coding for polypeptide F4617 having the amino acid sequence as shown by SEQ ID NO:1 wherein the 1-8th amino acid sequence is replaced by the amino acid sequence shown by SEQ ID NO:2, and the 106th Gly is replaced by Trp.

Vector pKF 4630: coding for polypeptide F4630 having the amino acid sequence as shown by SEQ ID NO:1 wherein the 1-8th amino acid sequence is replaced by the amino acid sequence shown by SEQ ID NO:2, and the 106th Gly is replaced by Pro.

Vector pKF 4631: coding for polypeptide F4631 having the amino acid sequence as shown by SEQ ID NO:1 wherein the 1-8th amino acid sequence is replaced by the amino acid sequence shown by SEQ ID NO:2, and the 106th Gly is replaced by Ala.

Vector pKF 4636: coding for polypeptide F4636 having the amino acid sequence as shown by SEQ ID NO:1 wherein the 1-8th amino acid sequence is replaced by the amino acid sequence shown by SEQ ID NO:2, and the 106th Gly is replaced by Asp.

Vector pKF 4637: coding for polypeptide F4637 having the amino acid sequence as shown by SEQ ID NO:1 wherein the 1-8th amino acid sequence is replaced by the amino acid sequence shown by SEQ ID NO:2, and the 106th Gly is replaced by Arg.

Host $E.\ coli$ cells having the above expression vectors produce polypeptides showing antitumor activities. This was confirmed by a test in which a supernatant fraction obtained after the centrifugal separation of a suspension of sonicated $E.\ coli$ cells, was tested in accordance with the method of Example 15 given hereinafter.

(3) Five $\mu$g of the human TNF N-terminal mutein expression vector pKF 4419 (about 3.9 Kbp) obtained in Example 9 was dissolved in a medium salt buffer, in accordance with the method of Example 3, and digested with restriction endonuclease Sac I and Hind III, whereupon a DNA fragment of about 3.5 Kbp containing a replication origin and a transcriptional regulation region, was separated and purified by agarose gel electrophoresis (gel concentration: 1%). On the other hand, 5 $\mu$g of the human TNF mutein expression vector pKF 4268, pKF 4150, pKF 4222, pKF 4267, pKF 4123 or pKF 4223 obtained in the above step (1) was digested with restriction endonuclease Sac I and Hind III in the same manner as above, whereupon a DNA fragment of about 360 bp containing a human TNF mutein gene having the N-terminal portion deleted, was separated and purified.

The two DNA fragments obtained by the above methods, were ligated by means of T4 DNA ligase, in accordance with the method of Example 3, and the ligated DNA was introduced into competent cells of an $E.\ coli$ K-12 JM103 strain. From the transformants thus-obtained, a clone having the desired expression vector pKF 4618, pKF 4619, pKF 4632, pKF 4633, pKF 4640 or pKF 4641 (about 3.9 Kbp) for F4618, F4619, F4632, F4633, F4640 or F4641 was selected by confirming the digestion pattern with restriction endonuclease Sac I and Hind III and by examining the nucleotide sequence around the replaced sites derived from the mutein polypeptide.

The N-terminal mutein expression vector cloned in accordance with the above method, induces the expression of a novel physiologically active polypeptide having the following replacements in E. coli cells.

Vector pKF 4618: coding for polypeptide F4618 having the amino acid sequence as shown by SEQ ID NO:1 wherein the 1-8th amino acid sequence is replaced by the amino acid sequence shown by SEQ ID NO:4, and the 106th Gly is deleted.

Vector pKF 4619: coding for polypeptide F4619 having the amino acid sequence as shown by SEQ ID NO:1 wherein the 1-8th amino acid sequence is replaced by the amino acid sequence shown by SEQ ID NO:4, and the 106th Gly is replaced by Trp.

Vector pKF 4632: coding for polypeptide F4632 having the amino acid sequence as shown by SEQ ID NO:1 wherein the 1-8th amino acid sequence is replaced by the amino acid sequence shown by SEQ ID NO:4, and the 106th Gly is replaced by Pro.

Vector pKF 4633: coding for polypeptide F4633 having the amino acid sequence as shown by SEQ ID NO:1 wherein the 1-8th amino acid sequence is replaced by the amino acid sequence shown by SEQ ID NO:4, and the 106th Gly is replaced by Ala.

Vector pKF 4640: coding for polypeptide F4640 having the amino acid sequence as shown by SEQ ID NO:1 wherein the 1-8th amino acid sequence is replaced by the amino acid sequence shown by SEQ ID NO:4, and the 106th Gly is replaced by Asp.

Vector pKF 4641: coding for polypeptide F4641 having the amino acid sequence as shown by SEQ ID NO:1 wherein the 1-8th amino acid sequence is replaced by the amino acid sequence shown by SEQ ID NO:4, and the 106th Gly is replaced by Arg.

Host E. coli cells having the above expression vectors produce polypeptides showing antitumor activities. This was confirmed by a test in which a supernatant fraction obtained after the centrifugal separation of a suspension of sonicated E. coli cells, was tested in accordance with the method of Example 15 given hereinafter.

EXAMPLE 12

Cloning of Plasmid pUC119(B)-F4236

Figure 13:
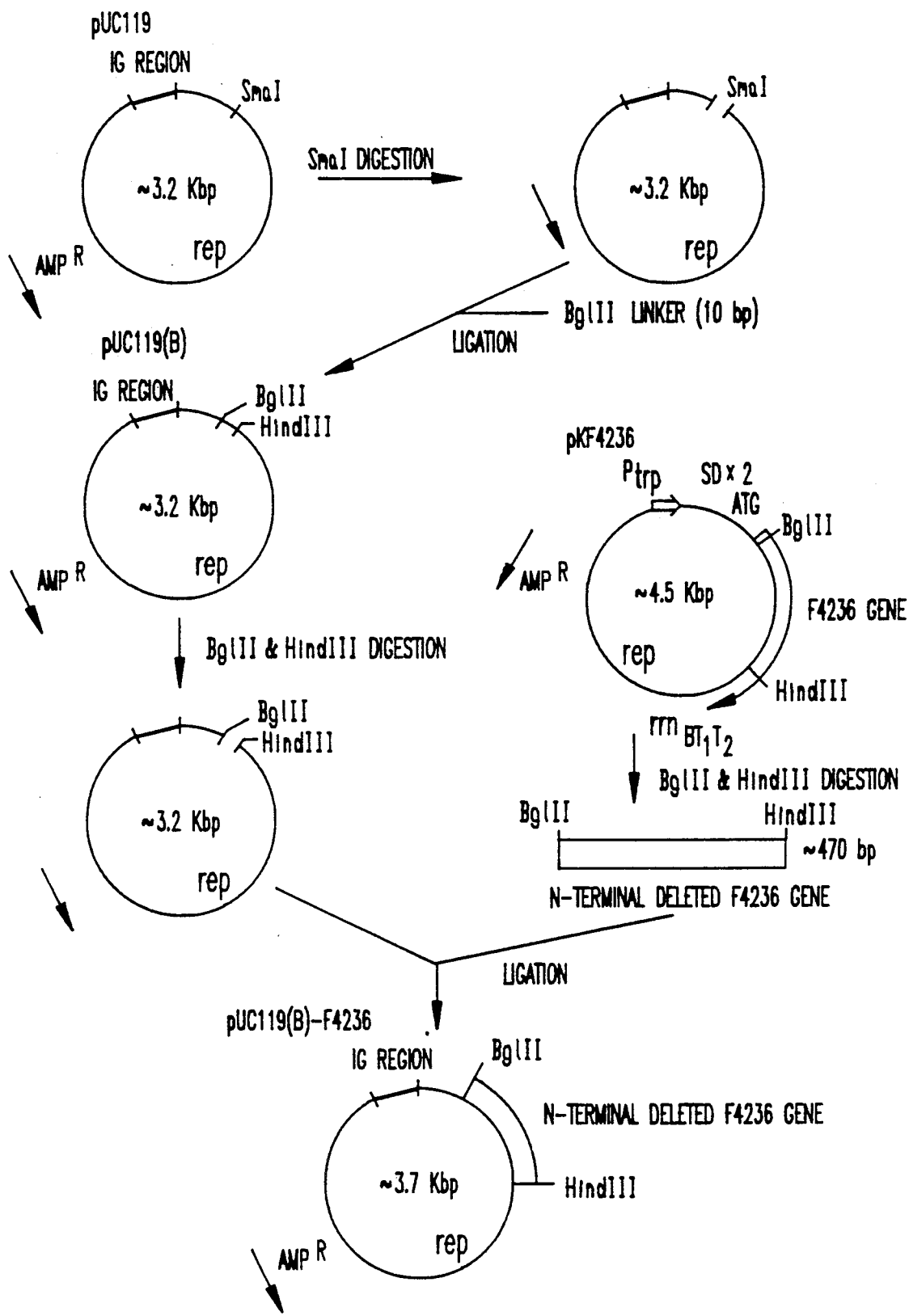
FIG. 13 illustrates the process steps for cloning plasmid pUC119(B)-F4236 containing a human TNF N-terminal mutein F4236 gene.

A method for cloning a plasmid (designated as pUC119(B)-F4236) having the human TNF N-terminal mutein F4236 gene inserted in plasmid vector pUC119 for the preparation of a single-stranded plasmid DNA, is illustrated schematically in FIG. 13.

One μg of plasmid vector pUC119 was dissolved in a Sma I buffer and digested with restriction endonuclease Sma I, in accordance with the method of Example 8(2). The obtained ring-opened plasmid was recovered by an ethanol precipitation operation, and 2 μg of non-phosphorylated Bgl II linker (Takara Shuzo) was inserted and ligated to the ring-opened site thereof by means of T4 DNA ligase, in accordance with the method of Example 4(1). From the transformants obtained in accordance with the method of Example 3, a clone having the desired plasmid pUC-119(B) (about 3.2 Kbp) having the restriction endonuclease Bgl II cleavage site newly inserted, was selected by examining the presence or absence of the cleavage site by the restriction endonuclease Bgl II with respect to the plasmid.

Then, 5 μg of plasmid pUC119(B) obtained above, was dissolved in a high salt buffer, in accordance with the method of Example 3, and digested with restriction endonuclease Bgl II and Hind III, and a DNA fragment of about 3.2 Kbp containing a replication origin was separated and purified by agarose gel electrophoresis (gel concentration: 1%).

On the other hand, 5 μg of human TNF N-terminal mutein expression vector pKF4236 (about 4.5 Kbp) obtained in Example 8, was digested with restriction endonuclease Bgl II and Hind III in the same manner as above, whereupon a DNA fragment of about 470 bp containing a F4236 gene having the N-terminal portion deleted, was separated and purified. The DNA fragment of about 470 bp was inserted and ligated to the previously purified DNA fragment of about 3.2 Kbp containing a replication origin by means of T4 DNA ligase, in accordance with the method described above. A clone having the desired plasmid pUC119(B)-F4236 (about 3.7 Kbp) was selected by confirming the digestion pattern with restriction endonuclease Bgl II and Hind III with respect to the plasmid, from the transformants obtained in accordance with the method of Example 3.

EXAMPLE 13

Cloning of human TNF N-terminal mutein expression vectors pKF 4620, pKF 4621, pKF 4622, pKF 4623, pKF 4624, pKF 4647, pKF 4648, pKF 4649, pKF 4650 and pKF 4651

(1) Primers 4134, 4391, 4392, 4409 and 4410 were designed. These primers are oligonucleotides comprising 1 bases having a nucleotide sequence of from the 76th T to the 96th T of SEQ ID NO:7 wherein the 85-87th 5'-CGC-3' is replaced by 5'-CAA-3' in the case of primer 4134, by 5'-AAG-3' in the case of primer 4391, by 5'-GAC-3' in the case of primer 4392, by 5'-GTC-3' in the case of primer 4409 and by 5'-CTC-3' in the case of primer 4410.

The chemical synthesis and purification of these oligonucleotides were conducted in accordance with the method of Example 2.

(2) A desired single-stranded plasmid DNA was prepared by using pUC119-F4419 obtained in Example 9 instead of pUC119-hTNF in Example 5 (1). Then, using this uracil-containing single-stranded plasmid DNA of pUC119-F4419 and primer 4134, 4391, 4392, 4409 or 4410 purified in the above step (1), the site-directed mutagenesis was conducted in accordance with the method of Example 5 (2) to obtain a plasmid (about 3.7 Kbp) containing DNA having the desired mutation introduced. It was confirmed by the dideoxy method that the mutation was introduced as designed, and this plasmid was designated as pUC119-F4620, pUC119-F4621, pUC119-F4622, pUC119-F4623 or pUC119-F4624. The desired human TNF N-terminal mutein gene obtained by the introduction of mutation, was inserted into expression vector pKK 101 containing tac promoter in accordance with the method of cloning a human TNF expression vector of Example 4, to obtain a human TNF N-terminal mutein expression vector. The human TNF N-terminal mutein gene (about 480 bp) was separated and purified after digestion of the plasmid pUC119-F4620, pUC119-F4621, pUC119-4622, pUC119-F4623 or pUC119-F4624 (about 3.7 Kbp) obtained above with restriction endonuclease EcoR I and Hind III in accordance with the above-mentioned method. The desired human TNF N-terminal mutein expression vector pKF 4620, pKF 4621, pKF 4622, pKF 4623 or pKF 4624 (about 3.9 Kbp) was obtained by using as the host an *E. coli* K-12 JM103 strain in the same manner as in the case of the human TNF expression vector (pKF 4102).

The N-terminal mutein expression vector cloned in accordance with the above method, induces the expression of a novel physiologically active polypeptide having the following replacements in *E. coli* cells.

Vector pKF 4620: coding for polypeptide F4620 having the amino acid sequence as shown by SEQ ID NO:1 wherein the 1-8th amino acid sequence is replaced by the amino acid sequence shown by SEQ ID NO:4, and the 29th Arg is replaced by Gln.

Vector pKF 4621: coding for polypeptide F4621 having the amino acid sequence as shown by SEQ ID NO:1 wherein the 1-8th amino acid sequence is replaced by the amino acid sequence shown by SEQ ID NO:4, and the 29th Arg is replaced by Lys.

Vector pKF 4622: coding for polypeptide F4622 having the amino acid sequence as shown by SEQ ID NO:1 wherein the 1-8th amino acid sequence is replaced by the amino acid sequence shown by SEQ ID NO:4, and the 29th Arg is replaced by Asp.

Vector pKF 4623: coding for polypeptide F4623 having the amino acid sequence as shown by SEQ ID NO:1 wherein the 1-8th amino acid sequence is replaced by the amino acid sequence shown by SEQ ID NO:4, and the 29th Arg is replaced by Val.

Vector pKF 4624: coding for polypeptide F4624 having the amino acid sequence as shown by SEQ ID NO:1 wherein the 1-8th amino acid sequence is replaced by the amino acid sequence shown by SEQ ID NO:4, and the 29th Arg is replaced by Leu.

Host *E. coli* cells having the above expression vectors produce polypeptides showing antitumor activities. This was confirmed by a test in which a supernatant fraction obtained after the centrifugal separation of a suspension of sonicated *E. coli* cells, was tested in accordance with the method of Example 15 given hereinafter.

(3) A desired single-stranded plasmid DNA was prepared by using pUC119(B)-F4236 obtained in Example 12 instead of pUC119-hTNF in Example 5 (1). Then, using this uracil-containing single-stranded plasmid DNA of pUC119(B)-F4236 and primer 4134, 4391, 4392, 4409 or 4410 purified in the above step (1), the site-directed mutagenesis was conducted in accordance with the method of Example 5 (2) to obtain a plasmid (about 3.7 Kbp) containing DNA having the desired mutation introduced. It was confirmed by the dideoxy method that the mutation was introduced as designed, and this plasmid was designated as pUC119-F4647, pUC119-F4648, pUC119-F4649, pUC119-F4650 or pUC119-F4651.

The novel human TNF N-terminal mutein gene obtained above, was inserted into expression vector pKF 4236 containing trp promoter to obtain a desired novel human TNF N-terminal mutein expression vector.

Five μg of the human TNF N-terminal mutein expression vector pKF 4236 (about 4.5 Kbp) obtained in Example 8 was digested with restriction endonuclease Bgl II and Hind III, in accordance with the method of Example 12, whereupon a DNA fragment of about 4.0 Kbp containing a replication origin and a transcriptional regulation region, was separated and purified by agarose gel electrophoresis (gel concentration: 1%). On the other hand, 5 μg of plasmid pUC119-F4647, pUC119-F4648, pUC119-F4649, pUC119-F4650 or pUC119-F4651 (about 3.7 Kbp) obtained above was digested with restriction endonuclease Bgl II and Hind III in the same manner as above, whereupon a DNA fragment of about 470 bp containing a human TNF N-terminal mutein gene having the N-terminal portion deleted, was separated and purified.

The two DNA fragments obtained by the above methods, were ligated by means of T4 DNA ligase, in accordance with the method of Example 3, and the ligated DNA was introduced into competent cells of an *E. coli* K-12 HB101 strain. From the transformants thus obtained, a clone having the desired expression vector pKF 4647, pKF 4648, pKF 4649, pKF 4650 or pKF 4651 (about 4.5 Kbp) for F4647, F4648, F4649, F4650 or F4651 was selected by confirming the digestion pattern with restriction endonuclease Bgl II and Hind III.

The N-terminal mutein expression vector cloned in accordance with the above method, induces the expression of a novel physiologically active polypeptide having the following replacements in *E. coli* cells.

Vector pKF 4647: coding for polypeptide F4647 having the amino acid sequence as shown by SEQ ID NO:1 wherein the 1-8th amino acid sequence is replaced by the amino acid sequence shown by SEQ ID NO:2, and the 29th Arg is replaced by Gln.

Vector pKF 4648: coding for polypeptide F4648 having the amino acid sequence as shown by SEQ ID NO:1 wherein the 1-8th amino acid sequence is replaced by the amino acid sequence shown by SEQ ID NO:2, and the 29th Arg is replaced by Lys.

Vector pKF 4649: coding for polypeptide F4649 having the amino acid sequence as shown by SEQ ID NO:1 wherein the 1-8th amino acid sequence is replaced by the amino acid sequence shown by SEQ ID NO:2, and the 29th Arg is replaced by Asp.

Vector pKF 4650: coding for polypeptide F4650 having the amino acid sequence as shown by SEQ ID NO:1 wherein the 1-8th amino acid sequence is replaced by the amino acid sequence shown by SEQ ID NO:2, and the 29th Arg is replaced by Val.

Vector pKF 4651: coding for polypeptide F4651 having the amino acid sequence as shown by SEQ ID NO:1 wherein the 1-8th amino acid sequence is replaced by the amino acid sequence shown by SEQ ID NO:2, and the 29th Arg is replaced by Leu.

Host *E. coli* cells having the above expression vectors produce polypeptides showing antitumor activities. This was confirmed by a test in which a supernatant fraction obtained after the centrifugal separation of a suspension of sonicated *E. coli* cells, was tested in accordance with the method of Example 15 given hereinafter.

EXAMPLE 14

Expression of human TNF polypeptide and human TNF N-terminal mutein polypeptide by *E. coli* and purification

*E. coli* K 12 JM103 strains having the human TNF expression vector (pKF 4102) obtained in Example 4 and the human TNF N terminal mutein expression vectors (pKF 4419, pKF 4146, pKF 4422 and pKF 4423) obtained in Examples 6, 7 and 9, were, respectively, inoculated to 20 ml of a M9 culture medium (0.6% Na$_2$HPO$_4$, 0.3% KH$_2$PO$_4$, 0.05% NaCl, 0.1% NH$_4$Cl, 2 mM MgSO$_4$, 0.2% glucose and 0.1 mM CaCl$_2$) containing from 25 to 50 µg/ml of ampicillin and 0.001% of vitamin B1 and cultured with shaking at 37° C. for 18 hours. Twenty ml of each cultured solution was added to 1 l of the above culture medium, followed by cultivation with shaking at 37° C. for from 2 to 3 hours. Then, isopropyl-β-D-thiogalactopyranoside (IPTG) was added so that the final concentration would be 1 mM, and the culturing was continued with shaking for a further 18 hours at 37° C.

E. coli K-12 HB101 strains having the human TNF N-terminal mutein expression vectors (pKF 4236, pKF 4603, pKF4616 and pKF 4617) obtained in Examples 8, 10 and 11, were inoculated to 20 ml of a M9CA culture medium (0.6% Na$_2$HPO$_4$, 0.3% KH$_2$PO$_4$, 0.05% NaCl, 0.1% NH$_4$Cl, 2 mM MgSO$_4$, 0.2% glucose and 0.1 mM CaCl$_2$ and 0.2% casamino acid) containing from 25 to 50 µg/ml of ampicillin, 0.001% of vitamin B1 and 5 µg/ml of tryptophan, and cultured at 37° C. for 18 hours with shaking. Twenty ml of this cultured solution was added to 1 l of the above culture medium not containing 5 µg/ml of tryptophan, and the culturing was conducted with shaking at 37° C. for 18 hours.

The E. coli cells were recovered by a centrifugal separation, and then the cells were washed by means of a TP buffer (10 mM Tris-HCl pH8.0 and 100 µM PMSF). After washing, the cells were suspended in the TP buffer in an amount of 10 volume (ml) per wet weight (g) of the cells, and the suspension was sonicated by means of a sonicator (Ultrasonic Proccesor, Model W-225 (Heat Systems, Ultrasonics Inc.)). The obtained suspension was subjected to centrifugal separation, and the debris was removed, and the supernatant fraction was recovered. The purification process subsequent to this sonicating treatment, was conducted mainly at a low temperature (0° to 4° C.).

This supernatant was filtered by a 0.45 µm filter and then fractionated by anion exchange chromatography (column size: φ 2.5×1.5 cm, flow rate: 0.5 ml/min) using Sepabeads FP-DA13 (Mitsubishi Chemical Industries Ltd.), whereupon an active fraction was recovered through identifying by SDS-polyacrylamide gel electrophoresis which will be described hereinafter and by determining the presence or absence of the activity in accordance with the method of Example 15 using L929 cells. For elution, TP buffer containing NaCl was employed, and the NaCl concentration was stepwise increased from 0.05M to 0.1M, 0.2M and 0.5M. The human TNF (1) was eluted with 0.1M NaCl, the human TNF (2) and the human TNF N-terminal muteins F4419, F4422, F4603, F4616 and F4617 were eluted with 0.2M NaCl, and the human TNF N-terminal muteins F4146 and F4236 were eluted with 0.5M NaCl. Further, in order to remove endotoxin, etc. derived from E. coli cells, treatment with nucleic acid endotoxin removing agent C-9 (manufactured by Kurita Water Industry Ltd. and sold by Dainippon Pharmaceutical Co., Ltd.) was conducted in accordance with the attached manual. Thus, partially purified samples of the human TNF polypeptides and the human TNF N-terminal mutein polypeptides were obtained.

Using these samples, evaluation of the antitumor activities and evaluation of the effects to experimental lung metastasis were conducted in Examples 15, 16 and 17. With respect to the N-terminal mutein polypeptide F4423, no active fraction was obtained probably because it is unstable in the host E. coli K-12 JM103 strain used. However, it may be possible to obtain the active fraction by using other host cells.

The above samples were filtered by a 0.20 µm filter, and then subjected to anion exchange chromatography using Mono Q (registered trademark) (HR 10/10 and HR 5/5) prepacked column (manufactured by Pharmacia LKB Biotechnology) under the control by a FPLC system and eluted with TPQ buffer (20 mM Tris-HCl pH8.0 and 10 µM PMSF) containing NaCl, whereupon active fractions were recovered through identifying by SDS-polyacrylamide gel electrophoresis which will be described hereinafter and by determining the presence or absence of the activity in accordance with the method of Example 15 employing L929 cells. The procedure of elution was conducted in accordance with the following program under the control by a FPLC system. The third step was repeated a few times until a single band was obtained by the SDS-polyacrylamide gel electrophoresis, in order to increase the purity by purification.

First step: Mono Q (registered trademark) (HR 10/10) column was used (flow rate: 4 ml/min)
 0-5 minutes: 0-0.2M NaCl linear gradient in concentration
 5-16 minutes: 0.2M NaCl
 16-20 minutes: 0.2-0.5M NaCl linear gradient in concentration
 20-24 minutes: 0.5M NaCl The fractionation results (NaCl concentration and retention time) of the active fractions in accordance with the above method were as follows: 0.2M, 6.6 minutes in the case of human TNF (1); 0.2M, 5.6 minutes in the case of human TNF (2); 0.2M, 6.5 minutes in the case of human TNF N-terminal mutein F4146; 0.2M, 6.4 minutes in the case of human TNF N-terminal mutein F4236; 0.2M, 5.4 minutes in the case of human TNF N-terminal mutein F4419; 0.2M, 7.6 minutes in the case of human TNF N-terminal mutein F4603; 0.2M, 5.0 minutes in the case of human TNF N-terminal mutein F4616; and 0.2M, 6.7 munites in the case of TNF N-terminal mutein F4617.

Second step: Mono Q (registered trademark) (HR 5/5) column was used (flow rate: 1 ml/min)
 0-2.5 minutes: 0-0.2M NaCl linear gradient in concentration
 2.5-8 minutes: 0.2M NaCl
 8-10 minutes: 0.2-0.5M NaCl linear gradient in concentration
 10-12 minutes: 0.5M NaCl The fractionation results (NaCl concentration and retention time) of the active fractions in accordance with the above method were as follows: 0.2M, 3.7 minutes in the case of human TNF (1); 0.2M, 4.1 minutes in the case of human TNF (2); 0.2M, 4.1 minutes in the case of human TNF N-terminal mutein F4146; 0.2M, 3.8 minutes in the case of human TNF N-terminal mutein F4236; 0.2M, 3.8 minutes in the case of human TNF N-terminal mutein F4419; 0.2M, 5.7 minutes in the case of human TNF N-terminal mutein F4603; 0.2M, 3.4 minutes in the case of human TNF N-terminal mutein F4616; and 0.2M, 4.4 munites in the case of TNF N-terminal mutein F4617.

Third step: Mono Q (registered trademark) (HR 5/5) column was used (flow rate: 1 ml/min)

0-6 minutes: 0-0.15M NaCl linear gradient in concentration 6-11 minutes: 0.15-0.2M NaCl linear gradient in concentration 11-13 minutes: 0.2-0.5M NaCl linear gradient in concentration 13-15 minutes: 0.5M NaCl The fractionation results (NaCl concentration and retention time) of the active fractions in accordance with the above method were as follows: 0.16M, 6.5 minutes in the case of human TNF (1); 0.16M, 6.5 minutes in the case of human TNF (2); 0.17M, 7.1 minutes in the case of human TNF N-terminal mutein F4146; 0.17M, 6.7 minutes in the case of human TNF N-terminal mutein F4236; 0.16M, 6.3 minutes in the case of human TNF N-terminal mutein F4419; 0.23M, 10.8 minutes in the case of human TNF N-terminal mutein F4603; 0.15M, 5.9 minutes in the case of human TNF N-terminal mutein F4616; and 0.18M, 8.7 munites in the case of TNF N-terminal mutein F4617.

Thus, purified samples of human TNF polypeptides and human TNF N-terminal mutein polypeptides were obtained. Using these samples, evaluation of the antitumor activities was conducted in the following Example 15. With respect to N-terminal mutein polypeptide F4422, deletion of the N-terminal portion was observed during the purification process, and therefore, the purification was stopped at that point.

Figure 14A:
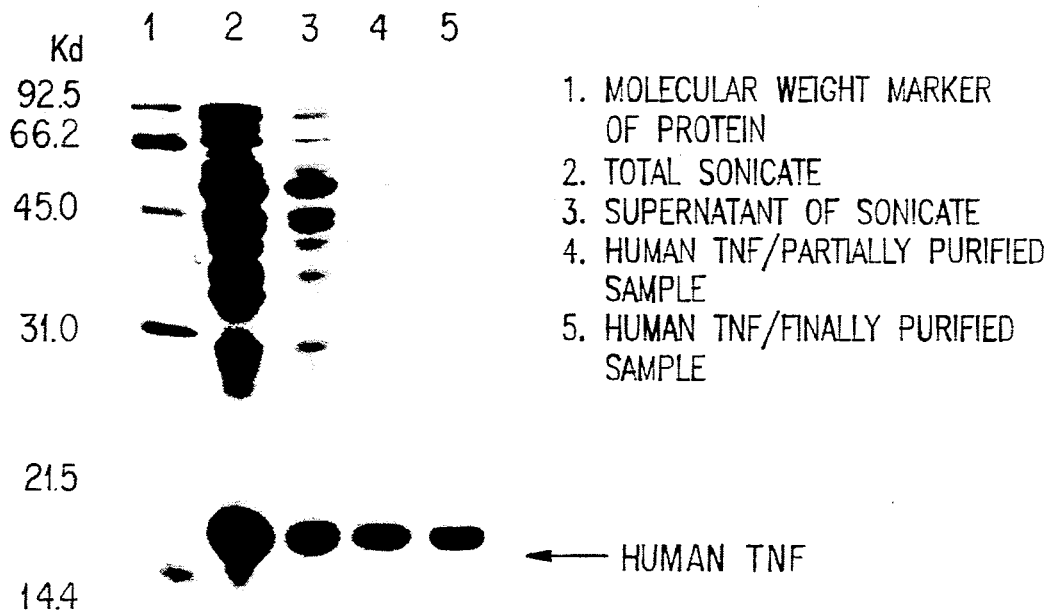
FIG. 14A-14B illustrates the results of electrophoresis of the purified samples of the human TNF polypeptide and the human TNF N-terminal mutein polypeptide expressed by *Escherichia coli.*
Figure 14B:
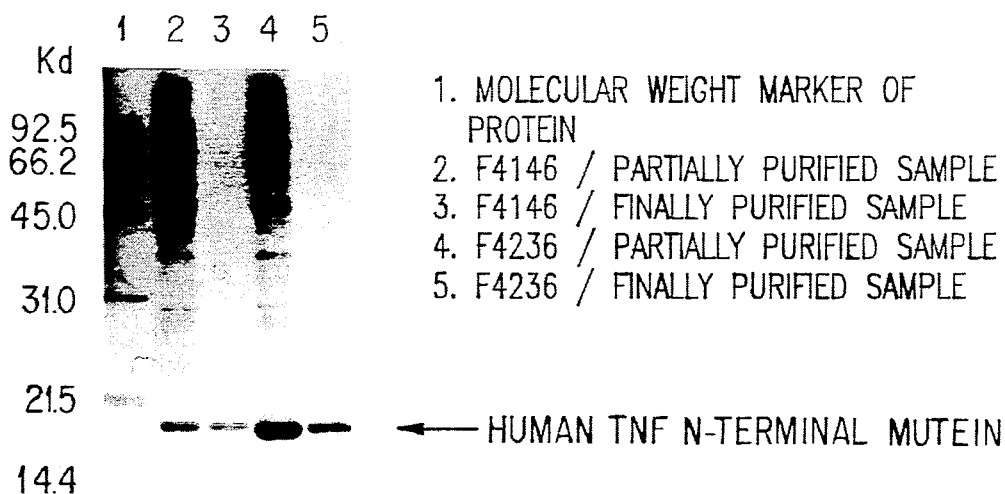
Figure 15A:
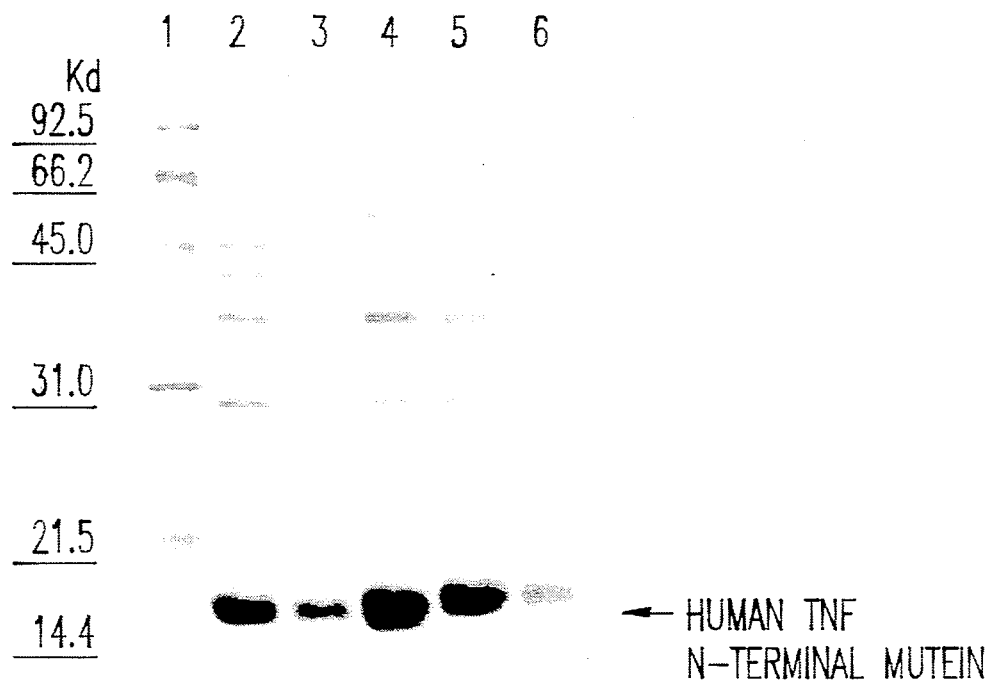
FIG. 15A-15B illustrates the results of electrophoresis of the purified samples of the human TNF N-terminal mutein polypeptide expressed by *Escherichia coli.*
Figure 15B:
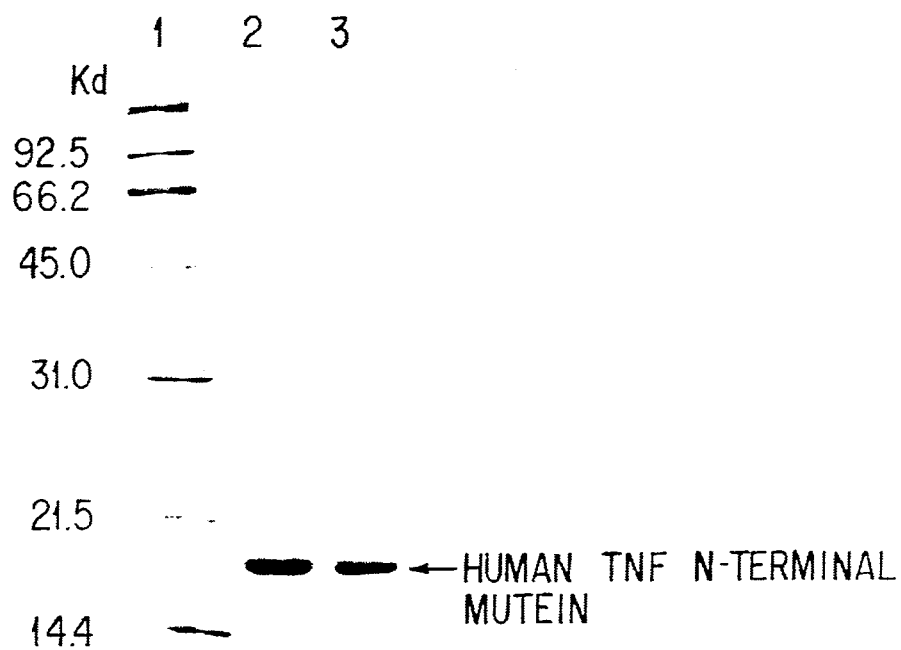

During the above purification and with respect to the purified samples, SDS-polyacrylamide gel electrophoresis was conducted to confirm the expression and purification of the human TNF polypeptides and the human TNF N-terminal mutein polypeptides. Each sample was added in a Laemmli's sample buffer (62.5 mM Tris-HCl pH6.8, 2% SDS, 0.01% BPB and 10% glycerol) containing 10 mM of DTT, and electrophoresis was conducted in accordance with the method of Laemmli (*Nature*, 227. 680 (1970)) using a 15% separation gel. After completion of the electrophoresis, the protein in the separation gel was confirmed by staining it with Coomassie Brilliant Blue. Some of the results are shown in FIGS. 14 and 15. The expression quantities by the respective expression vectors for the human TNF polypeptides and the human TNF N-terminal mutein polypeptides whereby active fractions were recovered, were substantially equal, and when the expression efficiency was calculated by subjecting the obtained stained gels to a chromatoscanner (CS-920 Model, manufactured by Shimadzu Corporation), it was found to be about 20% of the total cell proteins of *E. coli*. Further, each of the finally purified samples showed a single band in the obtained stained gel. From the migration positions, the molecular weights of the human TNF polypeptides and the human TNF N-terminal mutein polypeptides were calculated and shown in Table 1.

As one of the physical properties of proteins, isoelectric points of the human TNF polypeptides and the human TNF N-terminal mutein polypeptides were measured by an isoelectric focusing method using Ampholine (manufactured by LKB), and the results thereby obtained are shown in Table 1.

TABLE 1

Isoelectric points and molecular weights of human TNF polypeptide and human TNF N-terminal mutein polypeptide

| Polypeptide | Isoelectric point | Molecular weight (Kd) |
|---|---|---|
| Human TNF (1) | 5.6 | 17.0 |
| F4146 | 5.4 | 18.0 |
| F4236 | 5.6 | 17.7 |
| Human TNF (2) | 5.6 | 17.0 |
| F4419 | 5.6 | 17.0 |
| F4603 | 5.5 | 17.5 |
| F4616 | 5.6 | 17.7 |
| F4617 | 5.6 | 17.7 |

EXAMPLE 15

Evaluation of antitumor activities in vitro

With respect to the partially purified samples and finally purified samples of the human TNF polypeptides and the human TNF N-terminal mutein polypeptides obtained in Example 14, cell lytic activities against fibroblast cells (L929 (ATCC CCL1) derived from connective tissues of mouse), were determined in accordance with the method of Aggarwal et al. (*J. Biol. Chem.*, 260, 2345 (1985)). Namely, L929 cells were seeded on a 96-well microplate for tissue culture (manufactured by Corning) in an amount of $3 \times 10^4$ cells/0.1 ml/well and cultured overnight at 37° C in the presence of 5% carbon dioxide gas. As the culture medium, Dulbecco's modified Eagle's minimum essential medium (DME medium, manufactured by Sigma) containing 10% fetal calf serum, was used. Next day, the medium was changed to the above culture medium having Actinomycin D added to a final concentration of 1 μg/ml. Each sample diluted stepwisely by this culture medium, was applied to the respective wells (total amount of the medium: 0.1 ml). After culturing for a further 20 hours, live cells attached to the plate were stained with a 0.5% Crystal Violet solution (0.5% Crystal Violet/20% methanol) (at room temperature for 15 minutes). The plate having stained cells were thoroughly washed with a phosphate buffer PBS (10 mM Na.K phosphates pH7.4, 0.8% NaCl and 0.02% KCl) containing 1 mM of $CaCl_2$ and 1 mM of $MgCl_2$, and then Crystal Violet remained on the plate was extracted with 0.1 ml of a 0.01N HCl solution containing 30% ethanol, and then the absorbance (492 nm) was measured by an EIA reader (Model 2550, manufactured by Bio-Rad). This absorbance corresponds to the number of live cells. Therefore, the final dilution ratio of a sample at a well showing the absorbance corresponding to a 50% value of the absrobance of the well non-treated by the sample was obtained, and the reciprocal number of this dilution ratio of the sample is defined as the number of units per 1 ml of the sample (units/ml).

To calculate the specific activities (units/mg.protein) of the respective samples from the cell lytic activities (units/ml) against L929 obtained in accordance with the above method, the quantitative analysis of the proteins of the respective samples was conducted. The quantitative analysis was conducted in accordance with a Bradford method (*Anal. Biochem.*, 72, 248 (1976)), whereby the protein concentration (mg/ml) was obtained by using bovin serum albumin (BSA) as the standard sample. From these results, the specific activities were calculated with respect to the human TNF polypeptide samples and the human TNF N-terminal mutein polypeptide samples and shown in Table 2.

TABLE 2

Cell lytic activities against L929 of human TNF polypeptide and human TNF N-terminal mutein polypeptide

| Polypeptide | Specific activity (units/mg-protein) | |
|---|---|---|
| | Partially purified sample | Finally purified sample |
| Human TNF (1) | $2.7 \times 10^7$ | $8.0 \times 10^7$ |
| F4146 | $1.0 \times 10^6$ | $2.9 \times 10^7$ |
| F4236 | $1.3 \times 10^7$ | $2.3 \times 10^7$ |
| Human TNF (2) | $1.2 \times 10^7$ | $2.0 \times 10^7$ |
| F4419 | $1.4 \times 10^7$ | $1.7 \times 10^7$ |
| F4422 | $2.5 \times 10^6$ | — |
| F4603 | $1.1 \times 10^6$ | $2.7 \times 10^6$ |
| F4616 | — | $2.5 \times 10^7$ |
| F4617 | — | $3.9 \times 10^7$ |

From the above Table 2, it is apparent that the human TNF N-terminal mutein polypeptides of the present invention have cell lytic activities against fibroblast cells L929 derived from connective tissues of mouse, similar to that of the human TNF.

EXAMPLE 16

Evaluation of antitumor activities in vivo

With respect to the partially purified samples of the human TNF polypeptides and the human TNF N-terminal mutein polypeptides obtained in Example 14, the antitumor activities against a Meth A fibrosarcoma were determined. The test was conducted in such a manner that $1 \times 10^6$ cells/0.2 ml of Meth A fibrosarcoma cells (obtained from Sasaki Institutes, Sasaki Foundation) suspended in a saline were subcutaneously transplanted to the side part of the back of a BALB/C mouse (male, five weeks old, Charles River), and eight days later, after confirming that the tumor diameter reached a level of from 6 to 10 mm, a sample (0.2 ml/mouse) diluted stepwise with a saline was intravenously administered from the tail vein. The lethal dose was taken as the maximum dose, and samples of various doses were prepared by stepwise dilution.

For about two weeks after the administration, observation of tumor growth, etc. was continued. With respect to the tumor growth, the tumor volume $$\begin{pmatrix} ab^2/2: \\ a = \text{long diameter of the tumor} \\ b = \text{short diameter of the tumor} \end{pmatrix}$$

was measured, and the tumor volume ratio to the tumor volume after administration to the tumor volume on the day of administration of the sample (0 day) was obtained, whereby the number of days from 0 day when the tumor volume ratio became 2 or 5 (D2 or D5) was calculated. Then, the ratio to the control group (to which the saline was administered) was calculated, and the D2% control value and the D5% control value were obtained. The larger the values, the lower the tumor growing ability i.e. the higher the antitumor activities.

The results obtained in the above manner are shown in Tables 3 and 4.

TABLE 3

Antitumor activities of the human TNF polypeptide and the human TNF N-terminal mutein polypeptide against Meth A fibrosarcoma

| Poly-peptide | Dose (units/mouse) | Dose (μg/mouse) | Mortality (%) | Tumor volume ratio (%) D2% control | Tumor volume ratio (%) D5% control |
|---|---|---|---|---|---|
| Human TNF (1) | $2.0 \times 10^5$ | 7.4 | 22 | 562 | 251 |
| | $1.0 \times 10^5$ | 3.7 | 0 | 337 | 174 |
| F4146 | $2.5 \times 10^4$ | 25 | 0 | 164 | 202 |
| F4236 | $1.0 \times 10^5$ | 7.7 | 0 | 424 | 155 |
| | $5.0 \times 10^4$ | 3.8 | 0 | 463 | 166 |

(Note):
The mortality at a dose of $5.0 \times 10^4$ units/mouse of F4146 and the mortality at a dose of $2.0 \times 10^5$ units/mouse of F4236 were 100%.

TABLE 4

Antitumor activities of the human TNF polypeptide and the human TNF N-terminal mutein polypeptide against Meth A fibrosarcoma

| Poly-peptide | Dose (units/mouse) | Dose (μg/mouse) | Mortality (%) | Tumor volume ratio (%) D2% control | Tumor volume ratio (%) D5% control |
|---|---|---|---|---|---|
| Human TNF (2) | $2.0 \times 10^5$ | 17 | 67 | 438 | 220 |
| | $1.0 \times 10^5$ | 8.3 | 0 | 376 | 178 |
| | $5.0 \times 10^4$ | 4.1 | 0 | 245 | 139 |
| F4419 | $2.0 \times 10^5$ | 14 | 50 | 691 | 255 |
| | $1.0 \times 10^5$ | 7.1 | 0 | 447 | 208 |
| | $5.0 \times 10^4$ | 3.5 | 0 | 250 | 145 |
| F4422* | $1.5 \times 10^4$ | 6.0 | 0 | 477 | 220 |
| | $1.0 \times 10^4$ | 4.0 | 0 | 313 | 166 |
| | $5.0 \times 10^3$ | 2.0 | 0 | 220 | 131 |
| F4603 | $2.5 \times 10^4$ | 23 | 17 | 519 | 233 |
| | $1.0 \times 10^4$ | 9.1 | 0 | 286 | 147 |

(Note):
The mortality at a dose of $2.5 \times 10^4$ units/mouse of F4422 was 100%.

From Tables 3 and 4, it is evident that the human TNF N-terminal mutein polypeptides of the present invention have antitumor activities against Meth A fibrosarcoma transplanted to mouse, similar to that of the human TNF.

EXAMPLE 17

Effects against lung metastasis of tumor

By cloning B16F10 mouse melanoma cells (obtained from School of Medicine, Chiba University) by the following method, a clone showing a high level of metastasis to the lung was produced. Namely, $2\times 10^4$ cells/0.2 ml of B16F10 cells suspended in an Eagle's minimum essential medium (MEM medium, manufactured by Nissui Pharmaceutical Co., Ltd.), were injected into the tail vein of a C57BL/6 NCrj mouse (female, six weeks old, Charles River), and 14 days later, the lung was taken out. After washing the lung with a DME culture medium, one of metastatic nodules having a diameter of about 1 mm formed on the surface of the lung was sucked by a 26 G injection needle-attached syringe (manufactured by Termo) and suspended in 1 ml of the DME medium and cultured on a DME medium-containing soft agar containing 10% of fetal calf serum at 37° C in the presence of 5% carbon dioxide gas to form a colony. This colony formation method was conducted in accordance with the method disclosed in "Tissue Culturing Techniques" (p. 35–36, 1984, compiled by Japan Tissue Culture Association, Asakura Shoten). Ten to twelve days later, when the colony diameter reached a level of from 1 to 2 mm, the colony was sucked by a Pasteur pipet and cultured in a DME medium containing 10% of fetal calf serum. After the culturing, the proliferated cells were adjusted to a cell concentration of $2\times 10^4$ cells/0.2ml again by using the MEM medium and injected into the tail vein of a C57BL/6 NCrj mouse in the same manner as above. Fourteen days later, the lung was taken out, and one of metastatic nodules was isolated and cultured in the same manner as above. Such operation was repeated five times to obtain a clone (designated as B16F10/L5) resulting in a high level of metastasis to the lung.

The B16F10/L5 cells in a logarithmic phase cultured in the DME medium containing 10% of fetal calf serum by means of a dish for tissue culture having a diameter of 10 cm (Coning (registered trademark), manufactured by Iwaki Glass Co., Ltd.), were washed once with a phosphate buffer PBS in a state attached to the dish, and 5 ml of the MEM medium was added, followed by pipetting to obtain a cell suspension. The cells were collected by centrifugal separation and again suspended in 2 ml of the MEM medium. On the other hand, the partially purified samples of the human TNF polypeptides and the human TNF N-terminal mutein polypeptides obtained in Example 14 were diluted with the MEM medium to prescribed concentrations (the doses at which the antitumor effects were observed in the antitumor test in Example 16, were used as the doses for this test).

To this solution, the previously prepared B16F10/L5 cell suspension was added to prepare a cell suspension containing $2\times 10^4$ cells/0.2 ml of each partially purified sample solution. This cell suspension (0.2 ml/mouse) was injected into the tail vein of a C57BL/6 NCrj mouse (female, six weeks old). To the control group, only B16F10/L5 cells were injected. Fourteen days after the injection, the lung was taken out, and the number of metastatic nodules on the lung surface was counted.

The results obtained in the above manner are shown in Tables 5 and 6.

TABLE 5

Effects of human TNF N-terminal mutein polypeptide against lung metastasis of B16F10/L5 melanoma

| Polypeptide | Dose (units/mouse) | Dose (μg/mouse) | Number of lung metastatic nodules Average ± standard deviation (range) |
|---|---|---|---|
| Control | — | — | 2.8 ± 1.3 (1–4) |
| Human TNF (1) | $1.0 \times 10^5$ | 3.7 | 32.5 ± 9.3ⓒ (21–47) |
| F4146 | $2.5 \times 10^4$ | 25 | 0.5 ± 0.5 (0–1) |
| F4236 | $1.0 \times 10^5$ | 7.7 | 1.5 ± 1.1 (0–3) |

TABLE 6

Effects of human TNF N-terminal mutein polypeptides against lung metastasis of B16F10/L5 melanoma

| Exp. No. | Polypeptide | Dose (units/mouse) | Dose (μg/mouse) | Number of lung metastatic nodules Average ± standard deviation (range) |
|---|---|---|---|---|
| 1 | Control | — | — | 23.5 ± 2.6 (20–26) |
| | Human TNF (2) | $1.0 \times 10^5$ | 8.3 | 62.7 ± 4.6ⓒ (58–69) |
| | F4419 | $1.0 \times 10^5$ | 7.1 | 19.0 ± 4.1 (14–24) |
| 2 | Control | — | — | 12.8 ± 4.8 (6–19) |
| | Human TNF (2) | $5.0 \times 10^4$ | 4.1 | 40.3 ± 14.2ⓒ (25–63) |
| | F4603* | $2.5 \times 10^4$ | 23 | 8.8 ± 4.3 (5–16) |

(Note 1):
*F4291 (replacement of 68th Pro of human TNF by Asp) which is a different comparison to F4603, showed increasement of number of lung metastatic nudles, like human TNF.
(Note 2):
The dose adopted in this test was the dose which gave antitumor in the antitumor test in Example 16.
(Note 3):
ⓒSignificant difference observed at $P < 0.01$ as compared with the control group.

From Tables 5 and 6, it is evident that while the human TNF polypeptide and the human TNF mutein polypeptide have activities to promote experimental lung metastasis, the human TNF N-terminal mutein polypeptide of the present invention having an amino acid sequence of cell-adherent peptide of laminin introduced in the vicinity of the N-terminus, does not promote the experimental lung metastasis.

According to the present invention, a novel human TNF N-terminal mutein is provided which has the same antitumor activities as the human TNF or its mutein and which, on the other hand, does not have an activity to promote tumor-metastasis observed with the human TNF or its mutein, by substituting, on the human TNF or its mutein, the amino acid sequence of from the 1st Ser to the 8th Asp of SEQ ID NO:1 in the Sequence Listing or the corresponding amino acid sequence of the human TNF mutein by an amino acid sequence containing at least one amino acid sequence of cell-adherent peptide of laminin and from 5 to 30 amino acids.

Obviously, numerous modifications and variations of the present invention are possible in light of the above teachings. It is therefore to be understood that within the scope of the appended claims, the invention may be practiced otherwise than as specifically described herein.

What is claimed is:

1. A polypeptide which is a tumor necrosis factor polypeptide having an amino acid sequence represented by the sequence from the 1st Ser to the 155th Leu as shown in SEQ ID NO:1 in the Sequence Listing or the same amino acid sequence as such except that the 29th Arg, the 68th Pro or the 106th Gly is deleted or replaced by another amino acid residue, wherein the amino acid sequence of the 1st Ser to the 8th Asp of said SEQ ID NO: 1 is replaced by an amino acid sequence containing at least one amino acid sequence Tyr-Ile-Gly-Ser-Arg and from 11 to 17 amino acid residues.

2. The polypeptide of claim 1, having an amino acid sequence represented by the sequence from the 1st Ser to the 155th Leu as shown by SEQ ID NO: 1 in the Sequence Listing, wherein the amino acid sequence of the 1st Ser to the 8th Asp of said SEQ ID NO: 1 is replaced by an amino acid sequence containing at least one amino acid sequence Tyr-Ile-Gly-Ser-Arg and from 11 to 17 amino acid residues.

3. The polypeptide of claim 1, wherein in the sequence corresponding to the 9th Lys to the 155th Leu, said 29th Arg is deleted or replaced by Gln, Lys, Asp, Val or Leu; said 68th Pro is deleted or replaced by Asp or Met; or said 106th Gly is deleted or replaced by Trp, Pro, Ala, Asp or Arg.

4. The polypeptide of claim 1, which is selected from the group consisting of:
   a) the polypeptide of SEQ ID NO:1, wherein from the 1st Ser to the 8th Asp are replaced with the sequence of SEQ ID NO:3;
   b) the polypeptide of SEQ ID NO:1, wherein from the 1st Ser to the 8th Asp are replaced with the sequence of SEQ ID NO:2;
   c) the polypeptide of SEQ ID NO:1, wherein from the 1st Ser to the 8th Asp are replaced with the sequence of SEQ ID NO:4;
   d) the polypeptide of SEQ ID NO:1, wherein from the 1st Ser to the 8th Asp are replaced with the sequence of SEQ ID NO:5;
   e) the polypeptide of SEQ ID NO:1, wherein from the 1st Ser to the 8th Asp are replaced with the sequence of SEQ ID NO:2 and the 106th Gly is deleted;
   f) the polypeptide of SEQ ID NO:1, wherein from the 1st Ser to the 8th Asp are replaced with the sequence of SEQ ID NO:2 and the 106th Gly is replaced with Trp; and
   g) the polypeptide of SEQ ID NO:1, wherein from the 1st Ser to the 8th Asp are replaced with the sequence of SEQ ID NO:2 and the 68th Pro is replaced with Asp.

5. The polypeptide of claim 1, which is selected from the group consisting of:
   a) the polypeptide of SEQ ID NO:1, wherein from the 1st Ser to the 8th Asp are replaced with the sequence of SEQ ID NO:3;
   b) the polypeptide of SEQ ID NO:1, wherein from the 1st Ser to the 8th Asp are replaced with the sequence of SEQ ID NO:2;
   c) the polypeptide of SEQ ID NO:1, wherein from the 1st Ser to the 8th Asp are replaced with the sequence of SEQ ID NO:4;
   d) the polypeptide of SEQ ID NO:1, wherein from the 1st Ser to the 8th Asp are replaced with the sequence of SEQ ID NO:5;
   e) the polypeptide of SEQ ID NO:1, wherein from the 1st Ser to the 8th Asp are replaced with the sequence of SEQ ID NO:2 and the 68th Pro is replaced with Asp.

6. The polypeptide of claim 1, having a Met residue at the N-terminus position.

7. A pharmaceutical composition which comprises a pharmaceutically acceptable carrier and, as an active ingredient, a polypeptide which is a tumor necrosis factor polypeptide having an amino acid sequence represented by the sequence from the 1st Ser to the 155th Leu as shown by SEQ ID NO:1 in the Sequence Listing or the same amino acid sequence as such except that the 29th Arg, the 68th Pro or the 106th Gly is deleted or replaced by another amino acid residue, wherein the amino acid sequence of the 1st Ser to the 8th Asp of said SEQ ID NO:1 is replaced by an amino acid sequence containing at least one amino acid sequence Tyr-Ile-Gly-Ser-Arg and from 11 to 17 amino acid residues.

8. The pharmaceutical composition of claim 7, wherein said polypeptide has an amino acid sequence represented by the sequence from the 1st Ser to the 155th Leu as shown by SEQ ID NO:1 in the Sequence Listing, wherein the amino acid sequence of the 1st Ser to the 8th Asp of said SEQ ID NO:1 is replaced by an amino acid sequence containing at least one amino acid sequence Tyr-Ile-Gly-Ser-Arg and from 11 to 17 amino acid residues.

9. The pharmaceutical composition of claim 7, wherein in said polypeptide in the sequence corresponding to the 9th Lys to the 155th Leu, said 29th Arg is deleted or replaced by Gln, Lys, Asp, Val or Leu; said 68th Pro is deleted or replaced by Asp or Met; or said 106th Gly is deleted or replaced by Trp, Pro, Ala, Asp or Arg.

10. The pharmaceutical composition of claim 7, wherein said polypeptide is selected from the group consisting of:
   a) the polypeptide of SEQ ID NO:1, wherein from the 1st Ser to the 8th Asp are replaced with the sequence of SEQ ID NO:3;
   b) the polypeptide of SEQ ID NO:1, wherein from the 1st Ser to the 8th Asp are replaced with the sequence of SEQ ID NO:2;
   c) the polypeptide of SEQ ID NO:1, wherein from the 1st Ser to the 8th Asp are replaced with the sequence of SEQ ID NO:4;
   d) the polypeptide of SEQ ID NO:1, wherein from the 1st Ser to the 8th Asp are replaced with the sequence of SEQ ID NO:5;
   e) the polypeptide of SEQ ID NO:1, wherein from the 1st Ser to the 8th Asp are replaced with the sequence of SEQ ID NO:2 and the 106th Gly is deleted;
   f) the polypeptide of SEQ ID NO:1, wherein from the 1st Ser to the 8th Asp are replaced with the sequence of SEQ ID NO:2 and the 106th Gly is replaced with Trp; and
   g) the polypeptide of SEQ ID NO:1, wherein from the 1st Ser to the 8th Asp are replaced with the sequence of SEQ ID NO:2 and the 68th Pro is replaced with Asp.

11. The pharmaceutical composition of claim 7, wherein said polypeptide is selected from the group consisting of:
   a) the polypeptide of SEQ ID NO:1, wherein from the 1st Ser to the 8th Asp are replaced with the sequence of SEQ ID NO:3;

b) the polypeptide of SEQ ID NO:1, wherein from the 1st Ser to the 8th Asp are replaced with the sequence of SEQ ID NO:2;

c) the polypeptide of SEQ ID NO:1, wherein from the 1st Ser to the 8th Asp are replaced with the sequence of SEQ ID NO:4;

d) the polypeptide of SEQ ID NO:1, wherein from the 1st Ser to the 8th Asp are replaced with the sequence of SEQ ID NO:5;

e) the polypeptide of SEQ ID NO:1, wherein from the 1st Ser to the 8th Asp are replaced with the sequence of SEQ ID NO:2 and the 68th Pro is replaced with Asp.

12. The pharmaceutical composition of claim 7, wherein said polypeptide has a Met residue at the N-terminus position.

* * * * *